(12) United States Patent
van de Ven et al.

(10) Patent No.: US 9,661,715 B2
(45) Date of Patent: *May 23, 2017

(54) SOLID STATE LIGHT EMITTING DEVICES INCLUDING ADJUSTABLE MELATONIN SUPPRESSION EFFECTS

(71) Applicant: Cree, Inc., Durham, NC (US)

(72) Inventors: Antony Paul van de Ven, Sai Kung (HK); Paul Kenneth Pickard, Acton, CA (US)

(73) Assignee: Cree, Inc., Durham, NC (US)

( * ) Notice: Subject to any disclaimer, the term of this patent is extended or adjusted under 35 U.S.C. 154(b) by 227 days.

This patent is subject to a terminal disclaimer.

(21) Appl. No.: 14/662,608

(22) Filed: Mar. 19, 2015

(65) Prior Publication Data

US 2015/0195885 A1   Jul. 9, 2015

Related U.S. Application Data

(63) Continuation of application No. 13/763,579, filed on Feb. 8, 2013, now Pat. No. 9,039,746.

(51) Int. Cl.
*H05B 33/08* (2006.01)
*A61N 5/06* (2006.01)
*A61M 21/00* (2006.01)

(52) U.S. Cl.
CPC ......... *H05B 33/0857* (2013.01); *A61M 21/00* (2013.01); *A61N 5/0618* (2013.01);
(Continued)

(58) Field of Classification Search
CPC ........... A61N 5/06; H01L 29/20; H01L 29/84; H01L 33/00; F21V 9/16
(Continued)

(56) References Cited

U.S. PATENT DOCUMENTS 4,918,497 A   4/1990   Edmond
4,996,862 A   3/1991   Schrors
(Continued)

FOREIGN PATENT DOCUMENTS

DE    10233050 A1   2/2004
EP    2489717 A1    8/2012
(Continued)

OTHER PUBLICATIONS

Dilaura, D. "Photopic and Scotopic Lumens—1: An Introduction," Visual-3d, retrieved Feb. 27, 2013 from http://www.visual-3d.com/Education/LightingLessons/Documents/PhotopicScotopicLumens_1.pdf, 2 pages.
(Continued)

*Primary Examiner* — William Thomson
*Assistant Examiner* — Victor Shapiro
(74) *Attorney, Agent, or Firm* — Withrow & Terranova, P.L.L.C.; Vincent K. Gustafson

(57) ABSTRACT

Solid state light emitting devices include multiple LED components providing adjustable melatonin suppression effects. Multiple LED components may be operated simultaneously according to different operating modes according to which their combined output provides the same or similar chromaticity, but provides melatonin suppressing effects that differ by at least a predetermined threshold amount between the different operating modes. Switching between operating modes may be triggered by user input elements, timers/clocks, or sensors (e.g., photosensors). Chromaticity of combined output of multiple LED components may also be adjusted, together with providing adjustable melatonin suppression effects at each selected combined output chromaticity.

21 Claims, 15 Drawing Sheets

(52) U.S. Cl.
CPC . *H05B 33/0806* (2013.01); *A61M 2021/0044* (2013.01); *A61M 2021/0083* (2013.01); *A61N 2005/0626* (2013.01); *A61N 2005/0652* (2013.01); *A61N 2005/0662* (2013.01)

(58) Field of Classification Search
USPC ....... 606/88; 257/89, 98, 415; 313/495, 501, 313/503; 362/84
See application file for complete search history.

(56) References Cited

U.S. PATENT DOCUMENTS

| | | |
|---|---|---|
| 5,027,168 A | 6/1991 | Edmond |
| 5,210,051 A | 5/1993 | Carter, Jr. |
| 5,338,944 A | 8/1994 | Edmond et al. |
| 5,359,945 A | 11/1994 | Buckner et al. |
| 5,393,993 A | 2/1995 | Edmond et al. |
| 5,416,342 A | 5/1995 | Edmond et al. |
| 5,523,589 A | 6/1996 | Edmond et al. |
| 5,604,135 A | 2/1997 | Edmond et al. |
| 5,631,190 A | 5/1997 | Negley |
| 5,739,554 A | 4/1998 | Edmond et al. |
| 5,803,579 A | 9/1998 | Turnbull et al. |
| 5,912,477 A | 6/1999 | Negley |
| 6,120,600 A | 9/2000 | Edmond et al. |
| 6,187,606 B1 | 2/2001 | Edmond et al. |
| 6,201,262 B1 | 3/2001 | Edmond et al. |
| 6,600,175 B1 | 7/2003 | Baretz et al. |
| 6,791,119 B2 | 9/2004 | Slater, Jr. et al. |
| 6,853,010 B2 | 2/2005 | Slater, Jr. et al. |
| 6,958,497 B2 | 10/2005 | Emerson et al. |
| 7,015,636 B2 | 3/2006 | Bolta |
| 7,095,056 B2 | 8/2006 | Vitta et al. |
| 7,213,940 B1 | 5/2007 | Van De Ven et al. |
| 7,234,844 B2 | 6/2007 | Bolta et al. |
| 7,456,499 B2 | 11/2008 | Loh et al. |
| 7,564,180 B2 | 7/2009 | Brandes |
| 7,568,816 B2 | 8/2009 | Brass et al. |
| 7,579,662 B2 | 8/2009 | Tanaka |
| 7,679,281 B2 | 3/2010 | Kim et al. |
| 7,901,107 B2 | 3/2011 | Van De Ven et al. |
| 7,906,789 B2 | 3/2011 | Jung et al. |
| 7,909,479 B2 | 3/2011 | Rooymans |
| 8,264,138 B2 | 9/2012 | Negley et al. |
| 8,506,612 B2 | 8/2013 | Ashdown |
| 8,643,038 B2 | 2/2014 | Collins et al. |
| 9,039,746 B2 | 5/2015 | van De Ven et al. |
| 2005/0127381 A1 | 6/2005 | Vitta et al. |
| 2006/0149607 A1 | 7/2006 | Sayers et al. |
| 2006/0221272 A1 | 10/2006 | Negley et al. |
| 2007/0075629 A1 | 4/2007 | Le Toquin et al. |
| 2007/0139923 A1 | 6/2007 | Negley et al. |
| 2007/0152797 A1 | 7/2007 | Chemel et al. |
| 2007/0158668 A1 | 7/2007 | Tarsa et al. |
| 2007/0170447 A1 | 7/2007 | Negley et al. |
| 2007/0223219 A1 | 9/2007 | Medendorp, Jr. et al. |
| 2007/0253209 A1 | 11/2007 | Loh et al. |
| 2007/0267983 A1 | 11/2007 | Van De Ven et al. |
| 2008/0012036 A1 | 1/2008 | Loh et al. |
| 2008/0121921 A1 | 5/2008 | Loh et al. |
| 2008/0173884 A1 | 7/2008 | Chitnis et al. |
| 2008/0179611 A1 | 7/2008 | Chitnis et al. |
| 2008/0198112 A1 | 8/2008 | Roberts |
| 2008/0308825 A1 | 12/2008 | Chakraborty et al. |
| 2009/0046453 A1 | 2/2009 | Kramer |
| 2009/0050907 A1 | 2/2009 | Yuan et al. |
| 2009/0050908 A1 | 2/2009 | Yuan et al. |
| 2009/0080185 A1 | 3/2009 | McMillan |
| 2009/0184616 A1 | 7/2009 | Van De Ven et al. |
| 2009/0303694 A1 | 12/2009 | Roth et al. |
| 2010/0079059 A1 | 4/2010 | Roberts et al. |
| 2010/0174345 A1 | 7/2010 | Ashdown |
| 2010/0220471 A1 | 9/2010 | Rooymans |
| 2010/0244740 A1 | 9/2010 | Alpert et al. |
| 2011/0037378 A1 | 2/2011 | Yagi et al. |
| 2011/0220929 A1 | 9/2011 | Collins et al. |
| 2011/0221330 A1 | 9/2011 | Negley et al. |
| 2012/0008326 A1 | 1/2012 | Jou |
| 2012/0206050 A1 | 8/2012 | Spero |
| 2013/0296976 A1 | 11/2013 | Maxik et al. |
| 2014/0228914 A1 | 8/2014 | Van De Ven et al. |

FOREIGN PATENT DOCUMENTS

| | | |
|---|---|---|
| JP | 2000022221 A | 1/2000 |
| JP | 2004071726 A | 3/2004 |
| JP | 2004080046 A | 3/2004 |
| JP | 2005005482 A | 1/2005 |
| JP | 2006245443 A | 9/2006 |
| JP | 2006261702 A | 9/2006 |
| JP | 2007173557 A | 7/2007 |
| JP | 2007258620 A | 10/2007 |
| JP | 2007266579 A | 10/2007 |
| WO | 0019546 A1 | 4/2000 |
| WO | 2006132533 A2 | 12/2006 |
| WO | 2008053012 A1 | 5/2008 |
| WO | 2012166791 A2 | 12/2012 |

OTHER PUBLICATIONS

Nizamoglu, S. et al., "High scotopic/photopic ratio white-light emitting diodes integrated with semiconductor nanophosphors of collodial quantum dots," Optics Letters, vol. 36, No. 10, May 15, 2011, Optical Society of America, 3 pages.

Pascale,D., "A Review of RGB Color Spaces," BabelColor, 2002-2003, retrieved from http://www.babelcolor.com/download/A%20review%20of%20RGB%20color%20spaces.pdf, 35 pages.

Extended European Search Report for European Patent Application No. 14749260.7, mailed Aug. 17, 2016, 7 pages.

Official Letter and Search Report for Taiwan Patent Application No. 103103805, issued Aug. 24, 2016, 7 pages.

Author Unknown, "Boeing lighting project may help astronauts sleep," The Philadelphia Inquirer, Jul. 29, 2012, retrieved from http://www.heraldnet.com/article/20120729/NEWS02/707299898/0/SEARCH, 2 pages.

Author Unknown, "What is Induction Lighting?" MHT Lighting, retrieved Feb. 27, 2013 from http://www.mhtlighting.com/resources/induction-education/, 4 pages.

Author Unknown, "White Paper: Better Vision with LED Lights: Scotopic and Photopic Lumens," My LED Lighting Guide, 2008-2011, 8 pages.

Allen, M. et al., "Spectrally Enhanced Lighting," 2011 USACE Infrastructure Systems Conference, Jun. 15, 2011, 34 pages.

Dilaura, D. "Photopic and Scotopic Lumens—1: An Introduction," Visual-3d, retrieved Feb. 27, 2013 from http:// www.visual-3d.com/Education/LightingLessons/Documents/PhotopicScotopicLumens_1.pdf, 2 pages.

Josefowicz, J. et al., "Vision & Exterior Lighting: Shining Some Light on Scotopic & Photopic Lumens in Roadway Conditions," LED Roadway Lighting, Nov. 2008, 12 pages.

Nizamoglu, S. et al., "High scotopiclphotopic ratio white-light emitting diodes integrated with semiconductor nanophosphors of collodial quantum dots," Optics Letters, vol. 36, No. 10, May 15, 2011, Optical Society of America, 3 pages.

Nizamoglu, S. et al., "White light generation using CdSe/ZnS core-shell nanocrystals hybridized with InGaN/GaN light emitting diodes," Nanotechnology, vol. 18, No. 6, Feb. 14, 2007, IOP Publishing, 6 pages.

Pascale,D., "A Review of RGB Color Spaces," BabelColor, 2002-2003, retrieved from http://www.babelcolor.com/download/A%20review%20of%20RGB%20color/%20spaces.pdf, 35 pages.

Rea, M.S. et al, "Circadian light," Journal of Circadian Rhythms, vol. 8, Feb. 13, 2010, 10 pages.

Thapan, K. et al., "An action spectrum for melatonin suppression: evidence for a novel non-rod, non-cone photoreceptor system in humans," Journal of Physiology, vol. 535, Aug. 15, 2001, pp. 261-267.

(56) References Cited

OTHER PUBLICATIONS

International Search Report and Written Opinion for PCT/US2014014173, mailed May 28, 2014, 11 pages.
Non-Final Office Action for U.S. Appl. No. 13/763,579, mailed Mar. 24, 2014, 30 pages.
Notice of Allowance for U.S. Appl. No. 13/763,579, mailed Dec. 8, 2014, 9 pages.
Notice of Allowability and Interview Summary for U.S. Appl. No. 13/763,579, mailed Feb. 23, 2015, 9 pages.
Translation of Official Letter and Search Report for Taiwanese Patent Application No. 103103805, mailed Jan. 25, 2016, 7 pages.
International Preliminary Report on Patentability for International Patent Application No. PCT/US2014/014173, mailed Aug. 20, 2015, 8 pages.

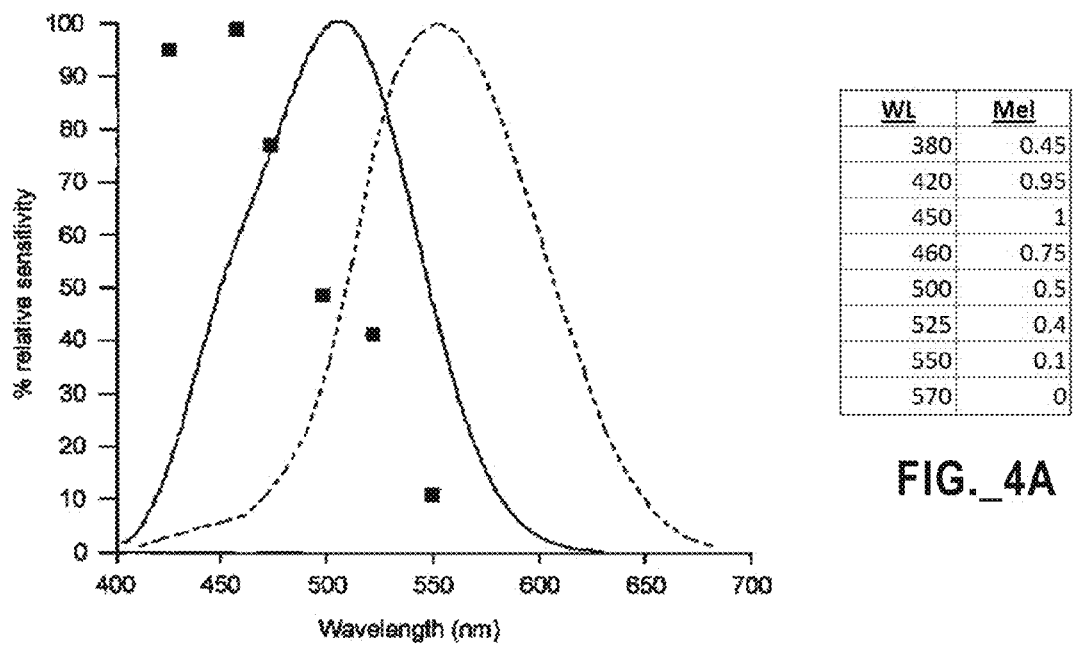
FIG._1
(RELATED ART)
FIG._4A
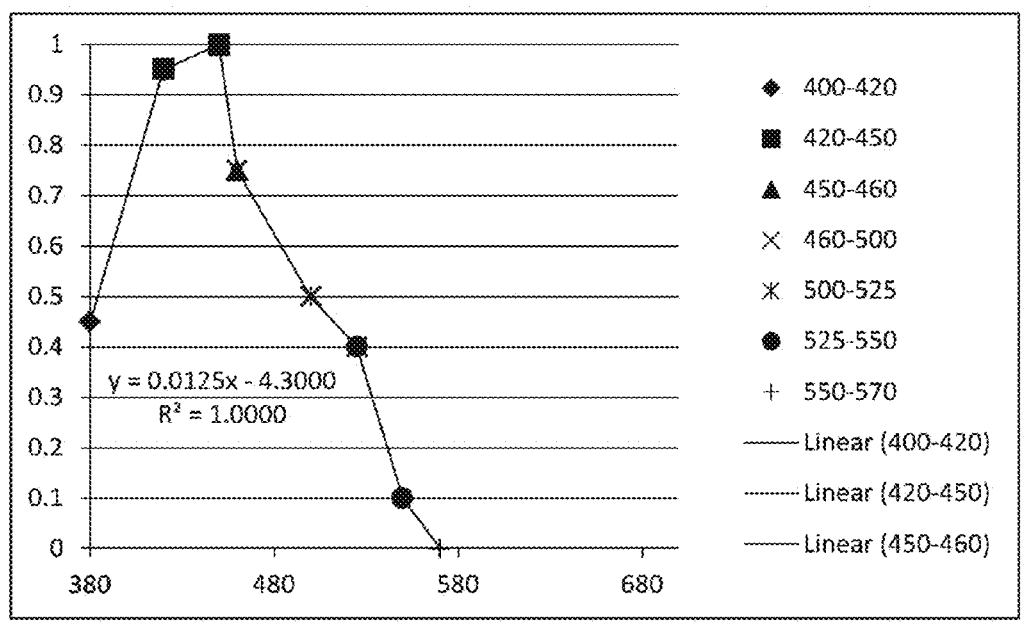
FIG._4B

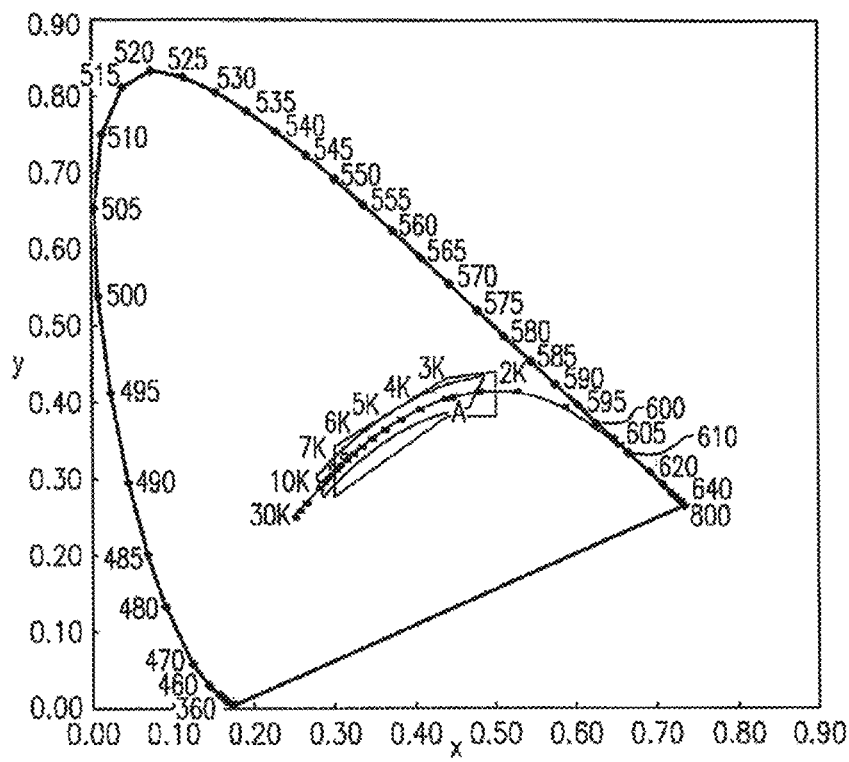
FIG._2
(RELATED ART)
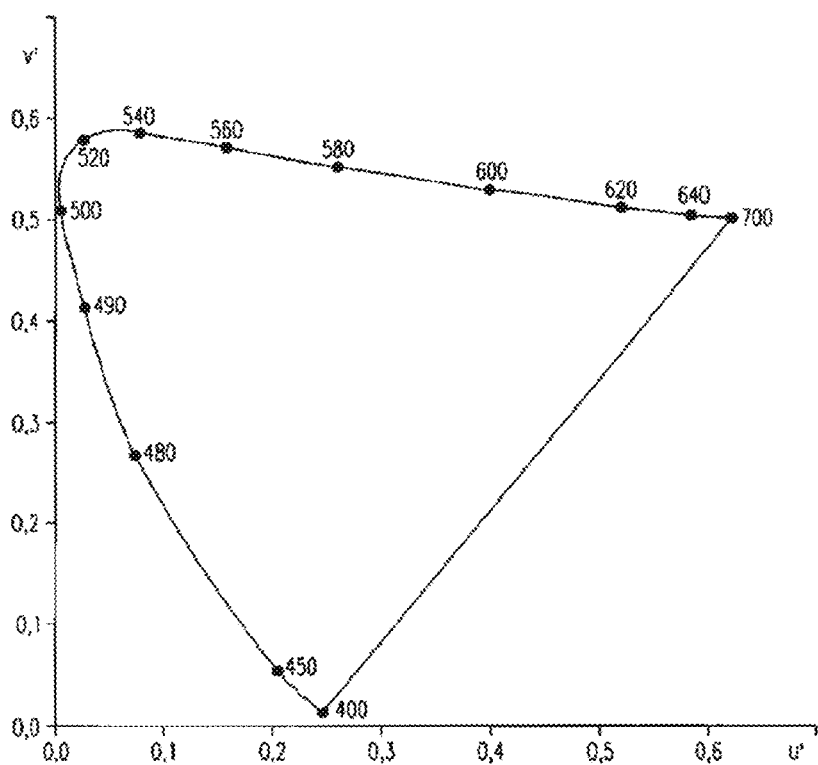
FIG._3
(RELATED ART)

| Light Source | CCT | CRI | Melatonin mw / 100Lumens | Notes |
|---|---|---|---|---|
| 60W Incandescent | 2725K | 100 | 54 | Full brightness (25 when dimmed) |
| TrueWhite® LED CR6 | 2725K | 93 | 46 | Full brightness (27 when dimmed to 2000K) |
| Warm White EasyWhite® LED | 2900K | 85 | 53 | |
| Metal Halide | 3000K | 87 | 72 | |
| Tri-phosphor Fluorescent | 3400K | 82 | 66 | |
| Standard Fluorescent | 4000K | 75 | 80 | |
| Cool White EasyWhite® LED | 4000K | 75 | 90 | |
| Sun on a white wall | 5000K | 99 | 120 | |
| Daylight Fluorescent | 5200K | 75 | 125 | |
| Blue Sky | 9000K | 98 | 200 | Very high total light |
FIG._5
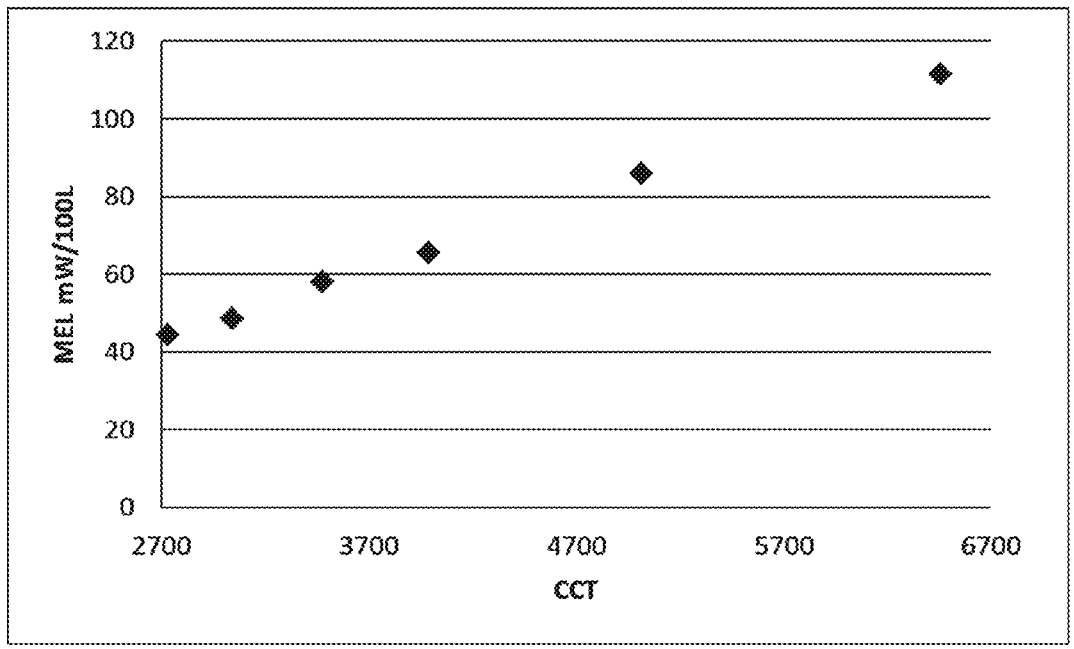
FIG._6

| Cyan + Red Lumens | BSY Lumens | Total Lumens | CRI | % BSY Lumens | Mel mW / 100Lumens |
|---|---|---|---|---|---|
| 497 | 0 | 497 | -22.6 | 0.0 | 89.5 |
| 512 | 85 | 597 | -0.8 | 14.2 | 84 |
| 502 | 160 | 662 | 14.6 | 24.2 | 79.5 |
| 489 | 295 | 784 | 35.1 | 37.6 | 72.4 |
| 465 | 499 | 964 | 56.5 | 51.8 | 65.6 |
| 434 | 633 | 1067 | 68.1 | 59.3 | 60.2 |
| 422 | 752 | 1174 | 75 | 64.1 | 58 |
| 436 | 947 | 1383 | 81.6 | 68.5 | 56 |
| 439 | 1125 | 1564 | 86.6 | 71.9 | 54.3 |
| 450 | 1726 | 2176 | 94.1 | 79.3 | 51 |
FIG._7A
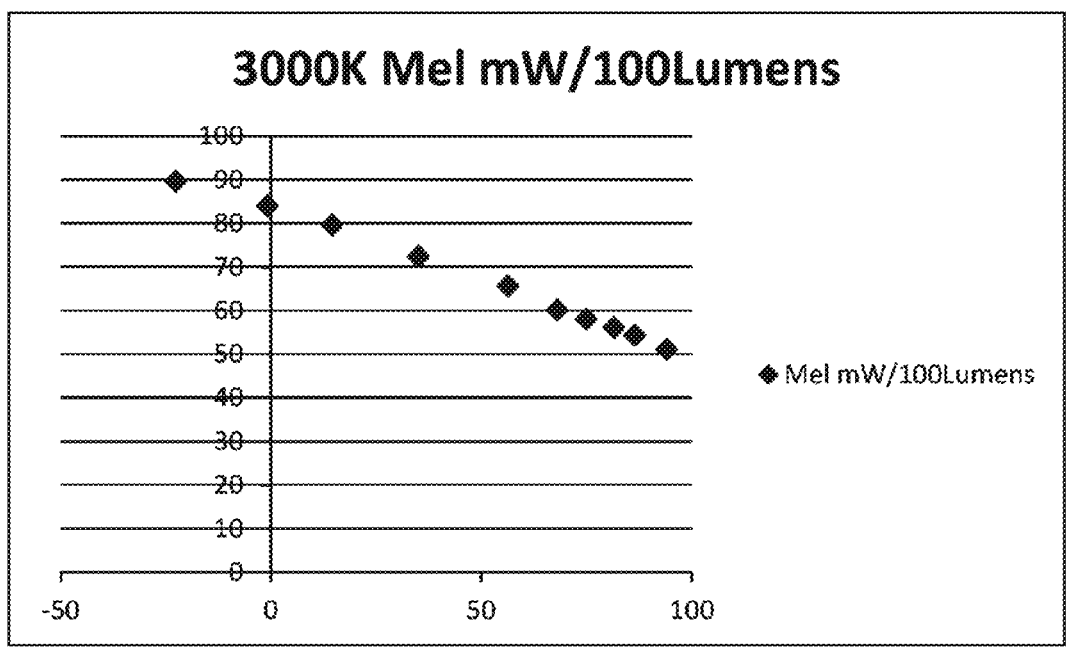
FIG._7B

| Cyan + Red Lumens | BSY Lumens | Total Lumens | CRI | % BSY Lumens | Mel mW / 100Lumens |
|---|---|---|---|---|---|
| 426 | 0 | 426 | -44.5 | 0.0 | 140.3 |
| 437 | 83 | 520 | -15.6 | 16.0 | 129.3 |
| 424 | 172 | 596 | 5.6 | 28.9 | 121.7 |
| 429 | 431 | 860 | 40.2 | 50.1 | 110.1 |
| 427 | 626 | 1053 | 55.6 | 59.4 | 104.7 |
| 427 | 814 | 1241 | 65.4 | 65.6 | 101 |
| 433 | 1223 | 1656 | 78.2 | 73.9 | 97.8 |
| 426 | 1495 | 1921 | 84.4 | 77.8 | 96 |
| 419 | 1758 | 2177 | 88.9 | 80.8 | 94.7 |
| 419 | 2936 | 3355 | 95.7 | 87.5 | 90.7 |
FIG._8A
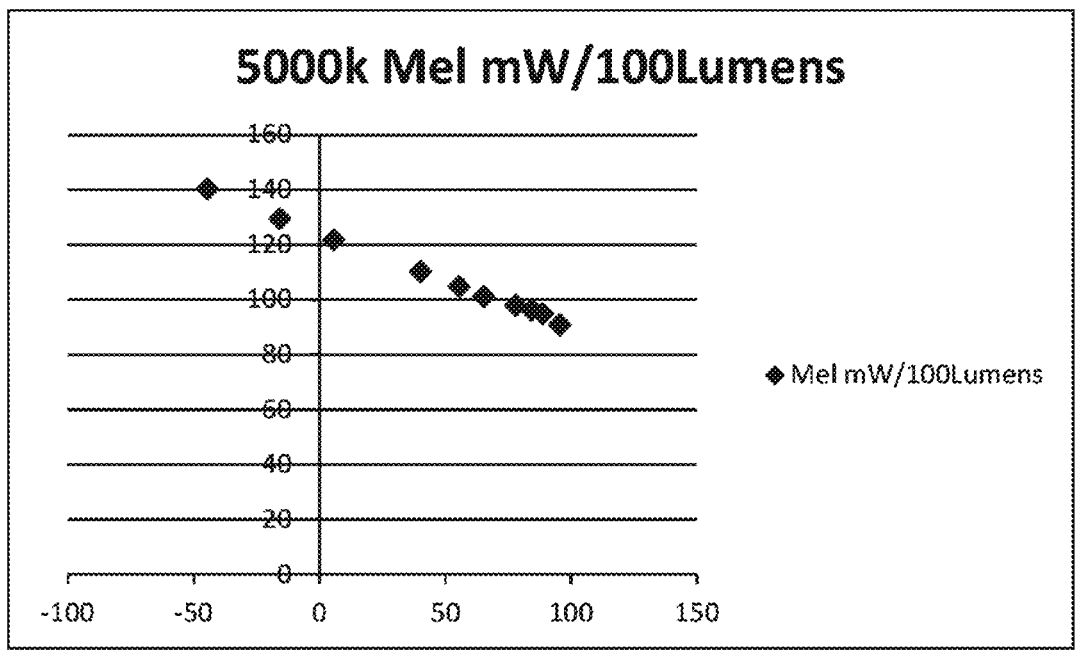
FIG._8B

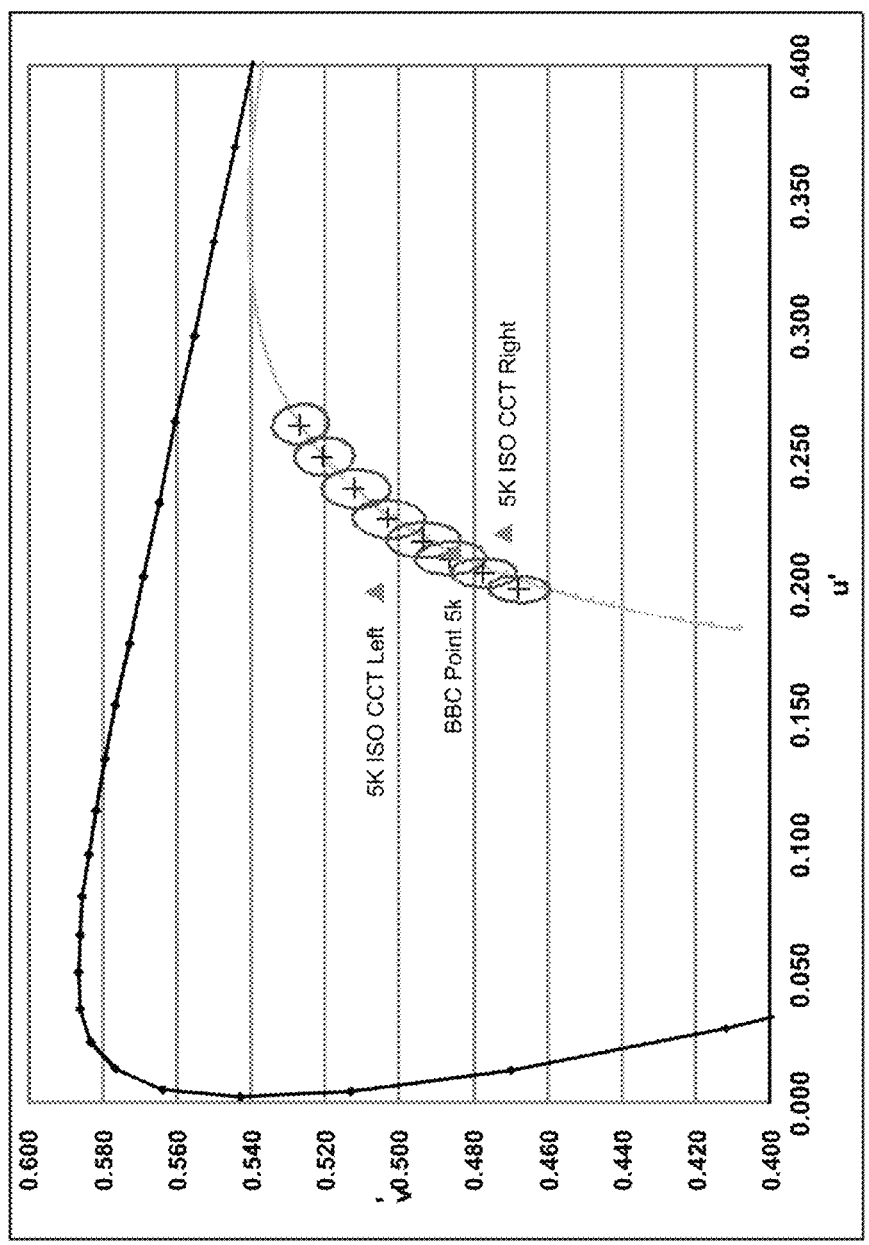
FIG._9B
FIG._9A

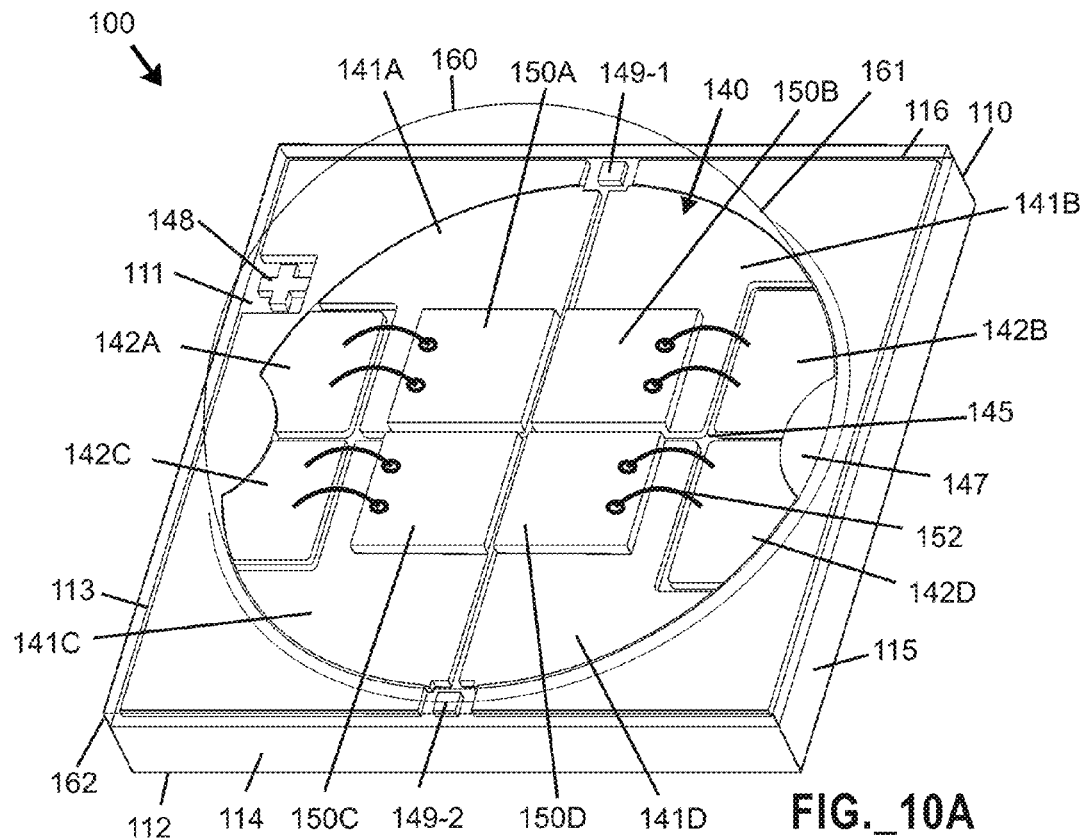
FIG._10A
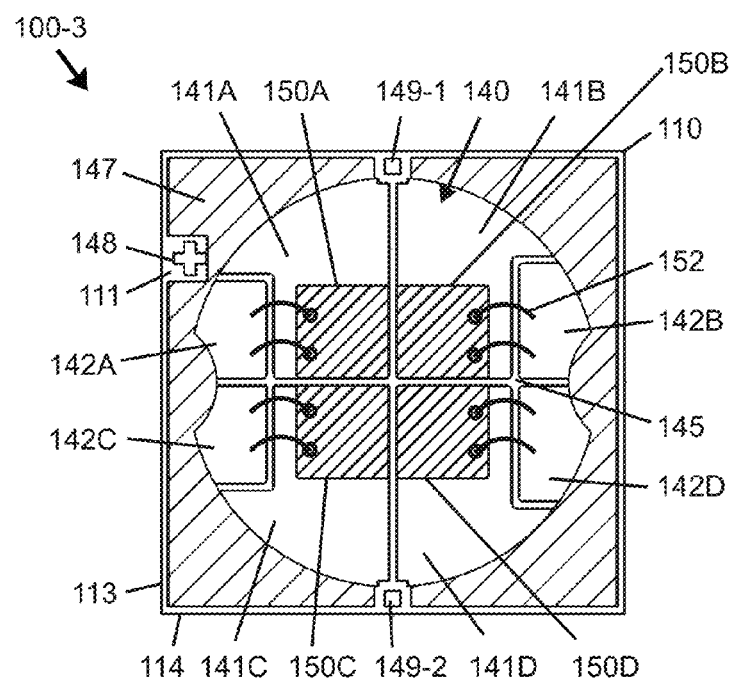
FIG._10B

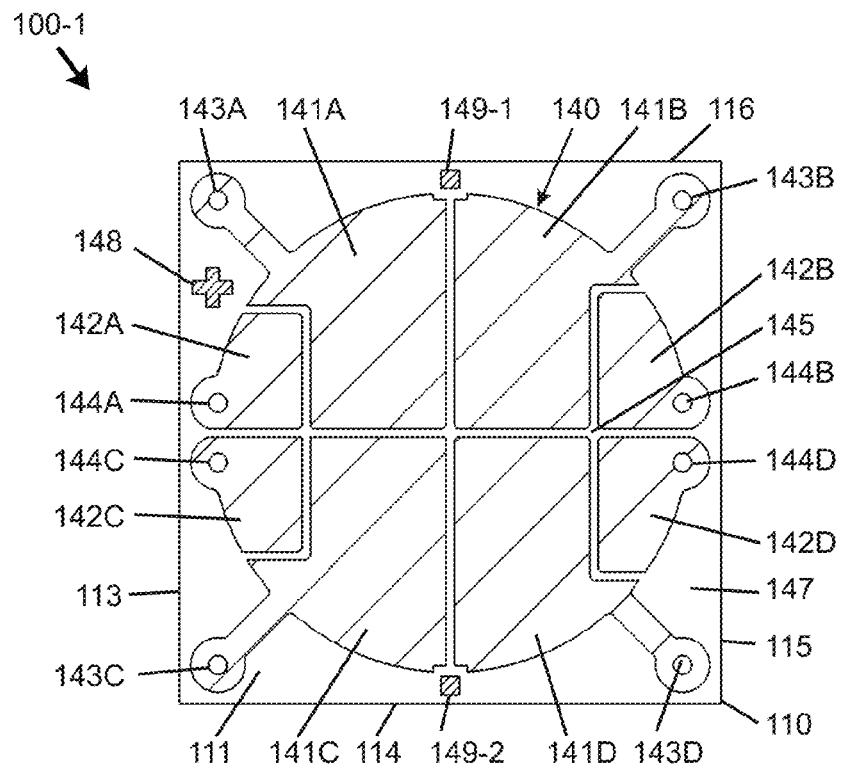
FIG._10C
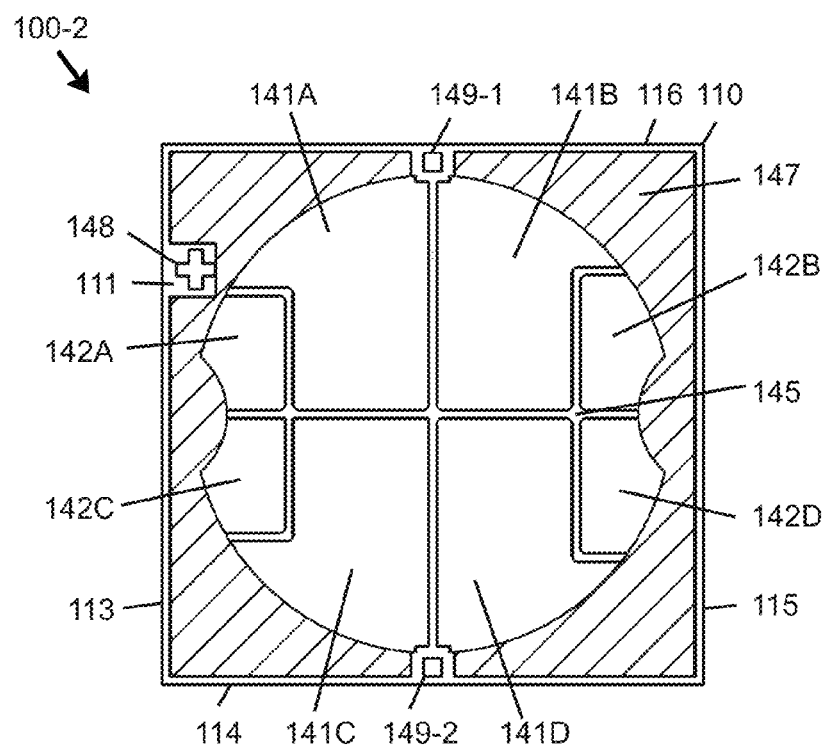
FIG._10D

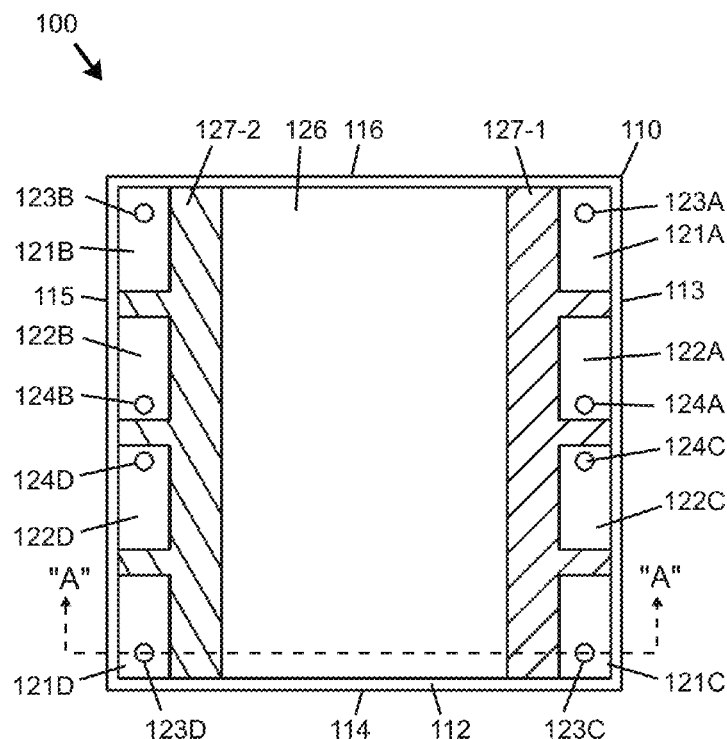
FIG._10E
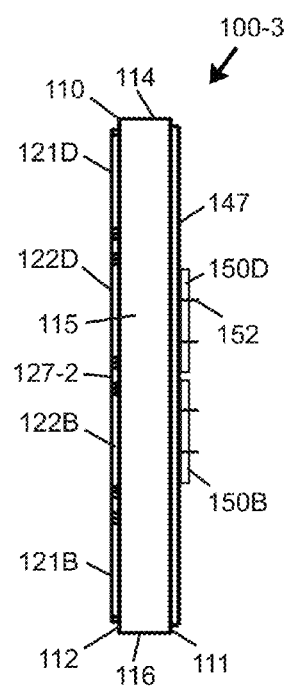
FIG._10F
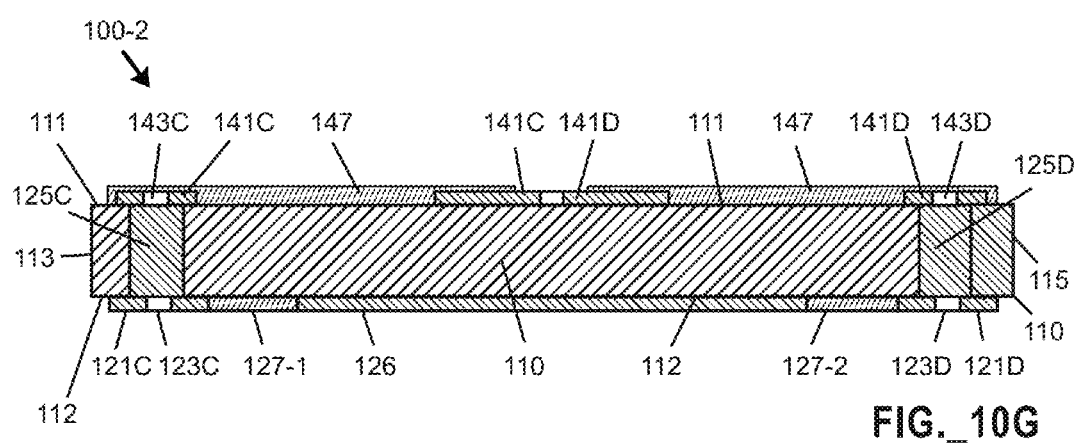
FIG._10G

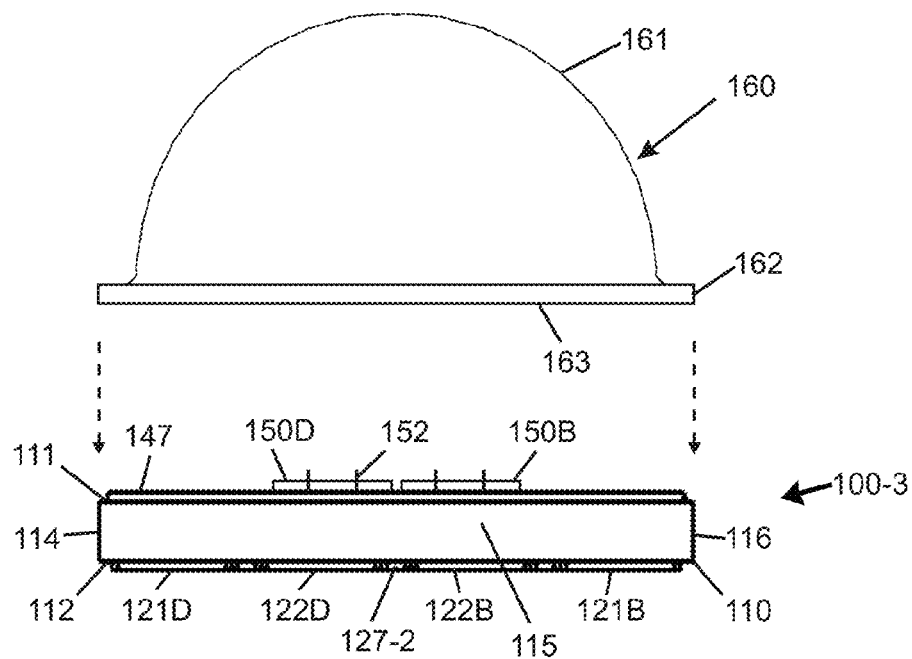
FIG._10H
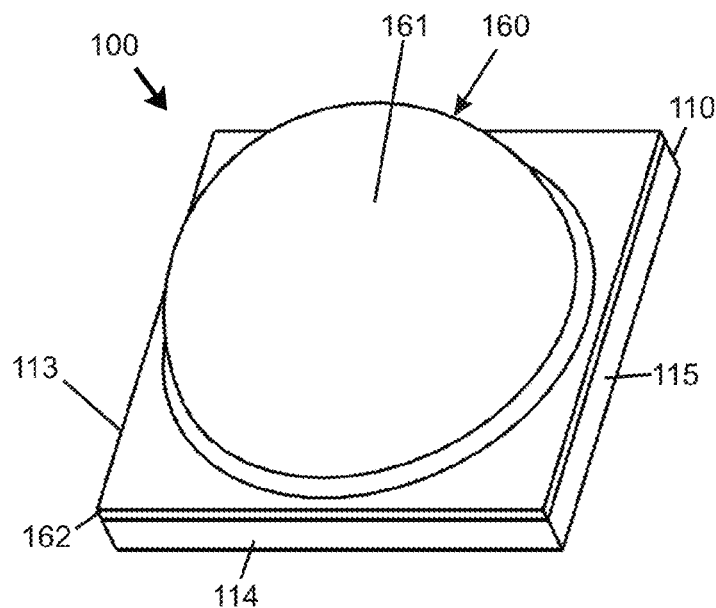
FIG._10I

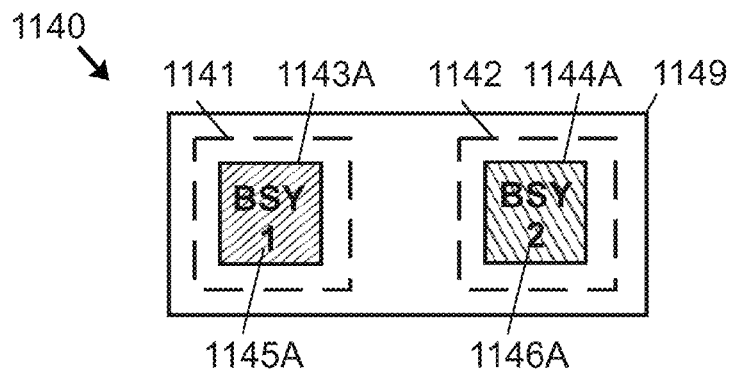
FIG. _11E
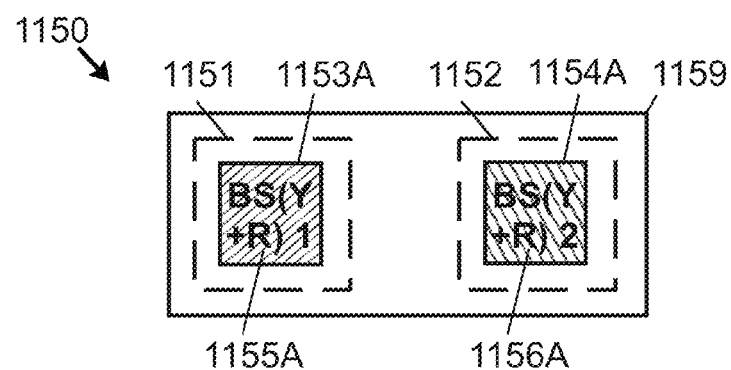
FIG. _11F
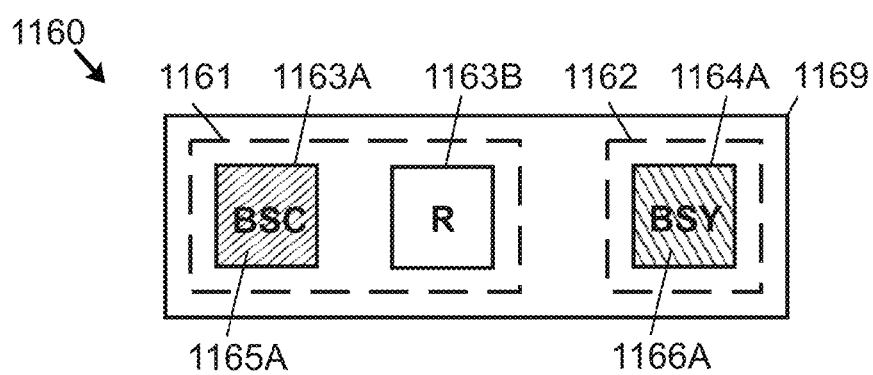
FIG. _11G
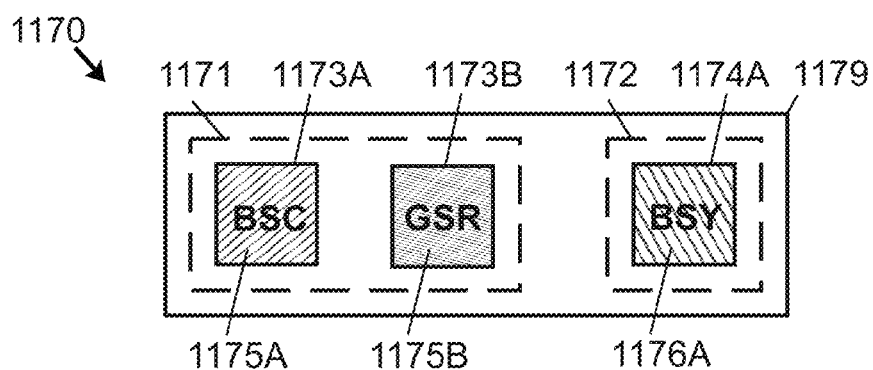
FIG. _11H

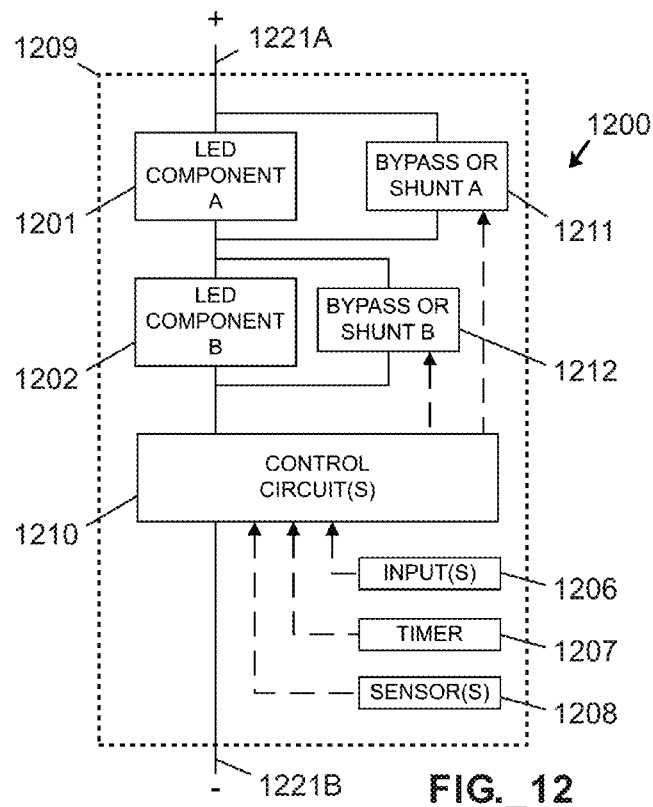
FIG._12
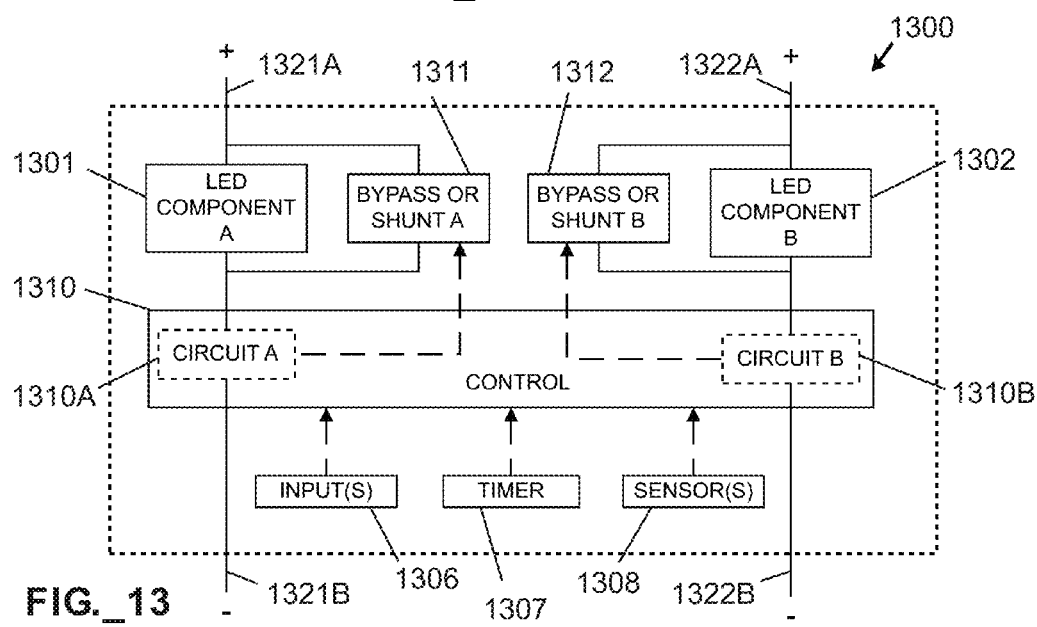
FIG._13

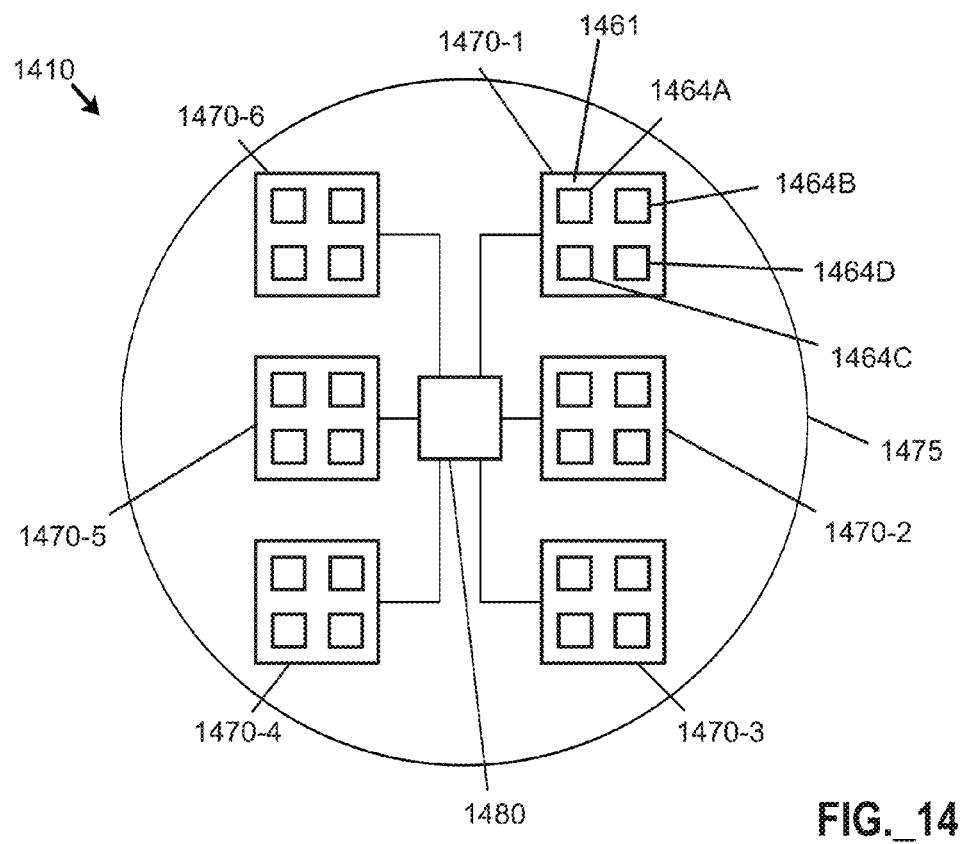
FIG._14
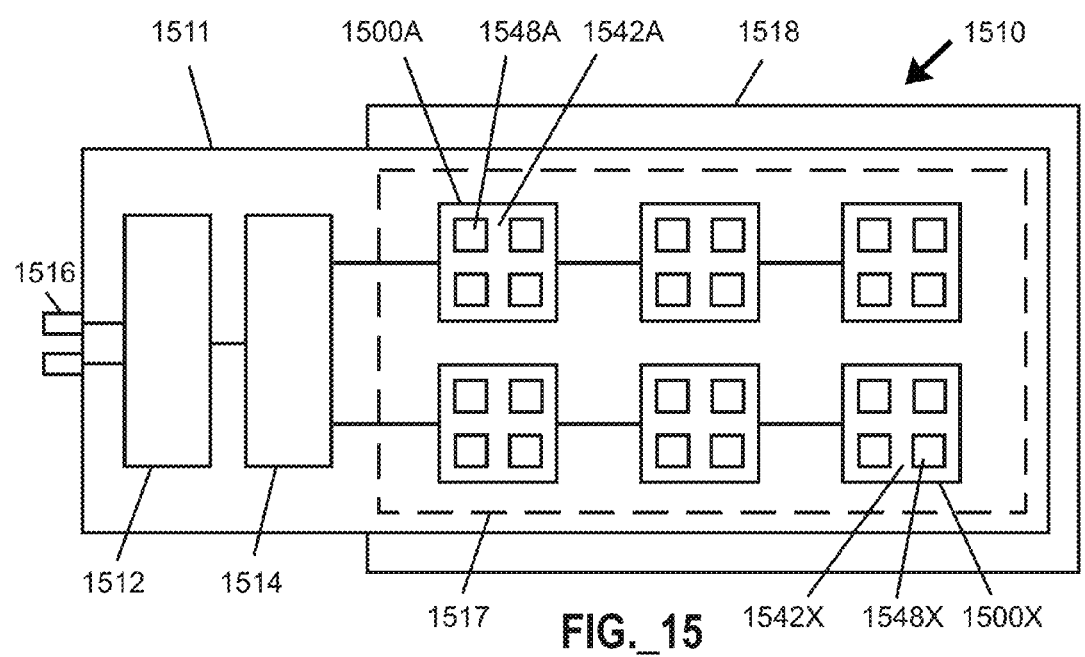
FIG._15

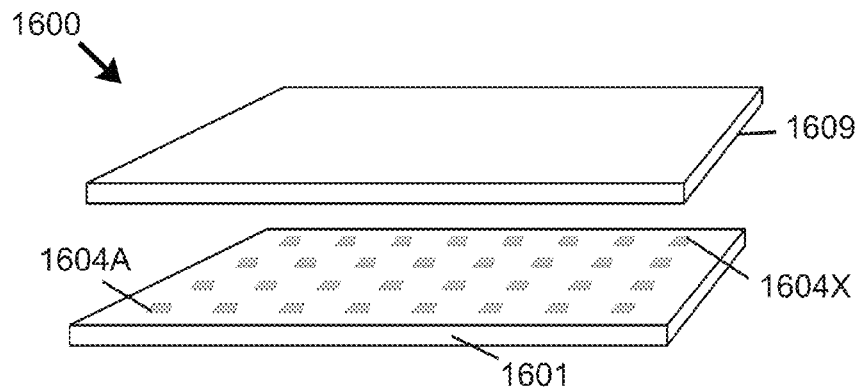
FIG._16
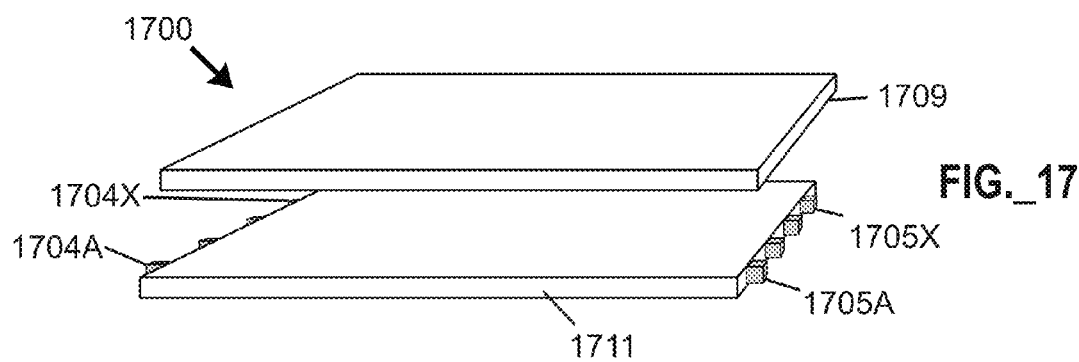
FIG._17
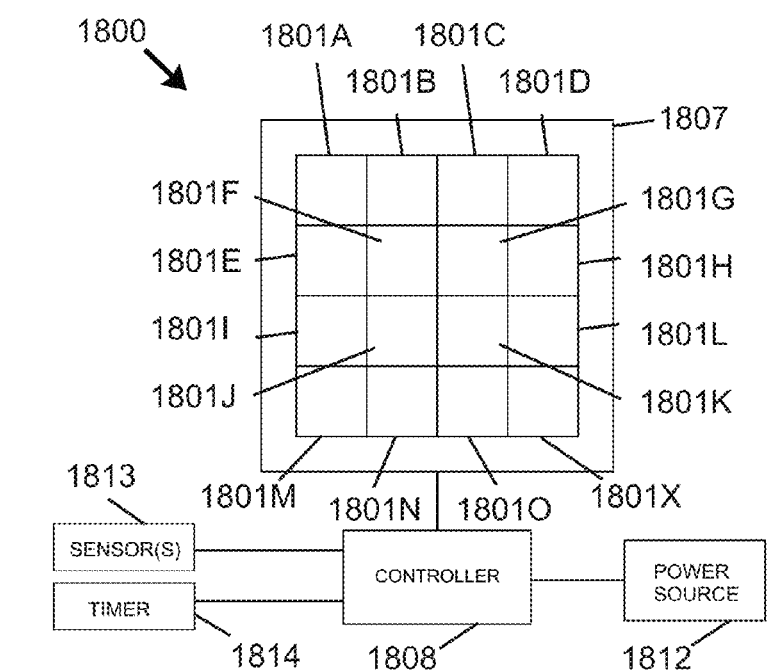
FIG._18

SOLID STATE LIGHT EMITTING DEVICES INCLUDING ADJUSTABLE MELATONIN SUPPRESSION EFFECTS

STATEMENT OF RELATED APPLICATION(S)

This application is a continuation of U.S. patent application Ser. No. 13/763,579 filed on Feb. 8, 2013 and subsequently issued as U.S. Pat. No. 9,039,746 on May 26, 2015. The disclosures of the foregoing application and patent are hereby incorporated by reference herein.

TECHNICAL FIELD

Subject matter herein relates to solid state lighting devices, including devices with different emitters or groups of emitters being controllable to permit adjustment of melatonin suppression effects, and relates to associated methods of making and using such devices.

BACKGROUND

In animals, circulating levels of the hormone melatonin (also known chemically as N-acetyl-5-methoxytryptamine) vary in a daily cycle, thereby allowing the entrainment of the circadian rhythms of several biological functions. Melatonin is produced in humans by the pineal gland, a small endocrine gland located in the center of the brain. The melatonin signal forms part of the system that regulates the sleep-wake cycle by chemically causing drowsiness and lowering the body temperature. Melatonin is commonly released in darkness (roughly 4-5 hours before sleep), and its production is suppressed by exposure to light. The light-dependent character of melatonin release and suppression aids in falling asleep and waking up. Depending on the amount, melatonin can reduce core body temperature and induce sleepiness. Conversely, nighttime light exposure can increase body temperature, and enhance alertness and performance.

It is principally blue light (e.g., including blue light at a peak wavelength value between 460 to 480 nm, with some activity from about 360 nm to about 600 nm), that suppresses melatonin and synchronizes the circadian clock, proportional to the light intensity and length of exposure. As shown in FIG. 1, the action spectrum for melatonin suppression (with six individual data points represented as black squares) shows short-wavelength sensitivity that is very different from the known spectral sensitivity of the scotopic response curve (represented with a solid line) and photopic response curve (represented with a dashed line)—being shifted approximately 50 nm and 100 nm to the left of the scotopic and photopic response, respectively. (FIG. 1 was originally presented in Thapan, Kavita, et al., "An action spectrum for melatonin suppression: evidence for a novel non-rod, non-cone photoreceptor system in humans," J. Physiol. (2001), 535.1, pp. 261-267.)

Circadian rhythm disorders may be associated with change in nocturnal activity (e.g., nighttime shift workers), change in latitude (e.g., jet lag), and/or seasonal change in light duration (e.g., seasonal affective disorder, with symptoms including depression). The World Health Organization in 2007 named late night shift work as a probable cancer-causing agent. Melatonin is an anti-oxidant and suppressant of tumor development; accordingly, interference with melatonin levels may increase likelihood of developing cancer. It would be desirable to ameliorate or reduce symptoms of circadian rhythm disorders and other health conditions that may be associated with reduced melatonin levels.

With proliferation of tablet computers, electronic readers, and other backlit electronic devices, consumers are increasingly utilizing backlit devices at nighttime hours, with the attendant potential for melatonin suppression. Some consumers have reported that reading textual content using backlight electronic devices reduces sensation of drowsiness and/or interferes with falling asleep normally, in a manner not experienced by reading conventional books. Although certain backlight devices (e.g., computer monitors) permit users to control backlight color temperature, certain backlight color temperatures are not aesthetically pleasing to certain users.

Solid state light sources such as organic or inorganic light emitting diodes (LEDs) or lasers may be used to provide colored (e.g., non-white) or white light (e.g., perceived as being white or near-white). White solid state emitters are increasingly being used potential replacements for white incandescent or fluorescent lamps for reasons including substantially increased efficiency and longevity. Solid state light sources provide potential for very high efficiency relative to conventional incandescent or fluorescent sources, but have presented challenges in simultaneously achieving good efficacy, good color reproduction, color variation among different emitters, and color stability (e.g., with respect to variations in operating temperature).

Color reproduction is commonly measured using Color Rendering Index (CRI) or average Color Rendering Index (CRI Ra). In calculating CRI, the color appearance of 14 reflective samples is simulated when illuminated by a reference illuminant and the test source, and a difference in color appearance for each sample between the test and reference illumination is computed. CRI therefore provides a relative measure of the shift in surface color and brightness of an object when lit by a particular lamp. The general color rendering index CRI Ra is a modified average utilizing the first eight indices, all of which have low to moderate chromatic saturation. The CRI Ra equals 100 (a perfect score) if the color coordinates and relative brightness of a set of test colors being illuminated by the illumination system are the same as the coordinates of the same test colors being irradiated by the reference radiator. Daylight has a high CRI (Ra of approximately 100), with incandescent bulbs also being relatively close (Ra greater than 95), and fluorescent lighting being less accurate (typical Ra of 70-80) for general illumination use where the colors of objects are not important. For some general interior illumination, a CRI Ra>80 is acceptable. CRI Ra>85, and more preferably, CRI Ra>90, provides greater color quality.

Aspects relating to the present inventive subject matter may be better understood with reference to the 1931 CIE (Commission International de l'Eclairage) Chromaticity Diagram and/or the 1976 CIE Chromaticity Diagram, both of which are well-known and readily available to those of ordinary skill in the art. The CIE Chromaticity Diagrams map out the human color perception in terms of two CIE parameters x and y (in the case of the 1931 diagram) or u' and v' (in the case of the 1976 diagram). The 1931 CIE Chromaticity Diagram is reproduced at FIG. 2, and the 1976 CIE Chromaticity Diagram (also known as (u'v') chromaticity diagram) is reproduced at FIG. 3. The spectral colors are distributed around the edge of the outlined space, which includes all of the hues perceived by the human eye. The boundary line represents maximum saturation for the spectral colors. The 1976 CIE Chromaticity Diagram is similar to the 1931 Diagram, except that the 1976 Diagram has been modified such that similar distances on the Diagram represent similar perceived differences in color. Since similar distances on the 1976 Diagram represent similar perceived differences in color, deviation from a point on the 1976 Diagram can be expressed in terms of the coordinates, u' and v', e.g., distance from the point=$(\Delta u'^2+\Delta v'^2)^{1/2}$, and the hues defined by a locus of points that are each a common distance from a specified hue consist of hues that would each be perceived as differing from the specified hue to a common extent.

The chromaticity coordinates (i.e., color points) that lie along the blackbody locus ("BBL") obey Planck's equation: $E(\lambda)=A\lambda^{-5}/(e^{B/T}-1)$, where E is the emission intensity, $\lambda$ is the emission wavelength, T the color temperature of the blackbody, and A and B are constants. Color coordinates that lie on or near the BBL yield pleasing white light to a human observer. The 1931 CIE Diagram (FIG. 2) includes temperature listings along the blackbody locus (embodying a curved line emanating from the right corner). These temperature listings show the color path of a blackbody radiator that is caused to increase to such temperatures. As a heated object becomes incandescent, it first glows reddish, then yellowish, then white, and finally bluish. This occurs because the wavelength associated with the peak radiation of the blackbody radiator becomes progressively shorter with increased temperature, consistent with the Wien Displacement Law. Illuminants which produce light that is on or near the BBL can thus be described in terms of their color temperature.

The term "white light" or "whiteness" does not clearly cover the full range of colors along the BBL since it is apparent that a candle flame and other incandescent sources appear yellowish, i.e., not completely white. Accordingly, the color of illumination may be better defined in terms of correlated color temperature (CCT) and in terms of its proximity to the BBL. The pleasantness and quality of white illumination decreases rapidly if the chromaticity point of the illumination source deviates from the BBL by a distance of greater than 0.01 in the x, y chromaticity system. This corresponds to the distance of about four MacAdam ellipses, a standard employed by the lighting industry. A lighting device emitting light having color coordinates that are within four MacAdam step ellipses of the BBL and that has a CRI Ra>80 is generally acceptable as a white light for illumination purposes. A lighting device emitting light having color coordinates within seven or eight MacAdam ellipses of the BBL and that has a CRI Ra>70 is used as the minimum standards for many other white lighting devices including compact fluorescent and solid state lighting devices. General illumination generally has a color temperature between 2,000 K and 10,000 K, with the majority of lighting devices for general illumination being between 2,700 K and 6,500 K.

The art continues to seek improved lighting devices that address one or more limitations inherent to conventional devices.

SUMMARY

The present invention relates in various aspects to solid state (e.g., LED) lighting devices including multiple solid state components providing adjustable melatonin suppression effects.

In one aspect, the invention relates to a light emitting apparatus comprising: a first LED component and a second LED component; wherein the first LED component and the second LED component are arranged to be operated in a first operating mode in which combined emissions of the first LED component and the second LED component (i) are within four MacAdam ellipses of a target correlated color temperature, and (ii) embody a first melatonin suppression milliwatt per hundred lumens value; wherein the first LED component and the second LED component are arranged to be operated in a second operating mode in which combined emissions of the first LED component and the second LED component (i) are within four MacAdam ellipses of the target correlated color temperature, and (ii) embody a second melatonin suppression per hundred lumens value that is at least about 10 percent greater than the first melatonin suppression per hundred lumens value; and wherein the light emitting apparatus comprises at least one of the following features (a) and (b): (a) at least one of the first LED component and the second LED component comprises at least one LED arranged to stimulate emissions of at least one lumiphoric material; and (b) combined emissions of the first LED component and the second LED component when operated in the first operating mode embody a color rendering index (CRI) value of at least about 80.

In another aspect, the invention relates to a light emitting apparatus comprising: a first LED component and a second LED component; wherein the first LED component and the second LED component are arranged to be operated at or near a first target correlated color temperature in a first operating mode in which combined emissions of the first LED component and the second LED component (i) are within four MacAdam ellipses of the first target correlated color temperature, and (ii) embody a first melatonin suppression milliwatt per hundred lumens value; wherein the first LED component and the second LED component are arranged to be operated at or near the first target correlated color temperature in a second operating mode in which combined emissions of the first LED component and the second LED component (i) are within four MacAdam ellipses of the first target correlated color temperature, and (ii) embody a second melatonin suppression per hundred lumens value that is at least about 10 percent greater than the first melatonin suppression per hundred lumens value; wherein the first LED component and the second LED component are arranged to be operated at or near a second target correlated color temperature in a third operating mode in which combined emissions of the first LED component and the second LED component (i) are within four MacAdam ellipses of the second target correlated color temperature, and (ii) embody a third melatonin suppression milliwatt per hundred lumens value; wherein the first LED component and the second LED component are arranged to be operated at or near the second target correlated color temperature in a fourth operating mode in which combined emissions of the first LED component and the second LED component (i) are within four MacAdam ellipses of the second target correlated color temperature, and (ii) embody a fourth melatonin suppression per hundred lumens value that is at least about 10 percent greater than the third melatonin suppression per hundred lumens value; and wherein the second target correlated color temperature differs from the first correlated color temperature preferably by at least about 300K (more preferably by at least about 600K, still more preferably by at least about 1000K).

In another aspect, the invention relates to a light fixture comprising a light emitting apparatus as disclosed herein, or an electronic device including a backlight comprising a light emitting apparatus as disclosed herein.

In another aspect, the invention relates to a method comprising illuminating an object, a space, or an environment, utilizing a light emitting apparatus as described herein.

In another aspect, the invention relates to a backlight arranged to illuminate a display panel arranged to display at least one of images and text, the backlight comprising: a first LED component; a second LED component; and a timer or clock arranged to trigger switching between a first operating mode and a second operating mode; wherein in the first operating mode the first LED component and second LED component generate combined emissions that (i) are within four MacAdam ellipses of a target correlated color temperature, and (ii) embody a first melatonin suppression milliwatt per hundred lumens value; and wherein in the second operating mode the first LED component and second LED component generate combined emissions that (i) are within four MacAdam ellipses of the target correlated color temperature, and (ii) embody a second melatonin suppression per hundred lumens value that is at least about 10 percent greater than the first melatonin suppression per hundred lumens value.

In another aspect, the invention relates to an electronic device comprising a backlight as disclosed herein and a display panel arranged to be illuminated by the backlight. In another aspect, the invention relates to a method comprising illuminating a display panel utilizing a backlight as disclosed herein.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Other aspects, features and embodiments of the invention will be more fully apparent from the ensuing disclosure and appended claims.

BRIEF DESCRIPTION OF THE DRAWINGS

FIG. 1 is a line chart showing superimposed plots of the visible light portion of the melatonin action spectrum (at left), the scotopic response curve (at center), and the photopic response curve (at right), depicting % relative sensitivity as a function of wavelength.

FIG. 2 is a 1931 CIE Chromaticity Diagram including representation of the blackbody locus, and further illustrating an approximately white area bounding the blackbody locus.

FIG. 3 is a 1976 CIE Chromaticity Diagram, also known as a (u'v') chromaticity diagram.

FIG. 4A is a table including values for the melatonin action spectrum (relative units) and corresponding wavelengths.

FIG. 4B is a line chart for melatonin action spectrum showing the values depicted in FIG. 4A.

FIG. 5 is a table including CCT, CRI, and melatonin suppressing milliwatts per 100 lumens values for various light sources.

FIG. 6 is a plot of melatonin suppressing milliwatts per 100 lumens versus CCT obtained by modeling a solid state light source including a blue LED arranged to stimulate emissions of a yellow lumiphor in combination with a red LED, showing increasing milliwatts per 100 lumens with increasing CCT.

FIG. 7A is a table identifying lumens, total lumens, relative lumens, CRI, and melatonin suppressing milliwatts per 100 lumens versus CRI at a CCT of 3000K obtained by modeling combined output of a first LED component including a blue LED arranged to stimulate emissions of a yellow lumiphor and a second LED component including a cyan LED arranged to stimulate emissions of a red lumiphor.

FIG. 7B is plot of melatonin suppressing milliwatts per 100 lumens versus CRI at a CCT of 3000K using data listed in the table of FIG. 7A.

FIG. 8A is a table identifying lumens, total lumens, relative lumens, CRI, and melatonin suppressing milliwatts per 100 lumens versus CRI at a CCT of 5000K obtained by modeling combined output of a first LED component including a blue LED arranged to stimulate emissions of a yellow lumiphor and a second LED component including a cyan LED arranged to stimulate emissions of a red lumiphor.

FIG. 8B is plot of melatonin suppressing milliwatts per 100 lumens versus CRI at a CCT of 5000K using data listed in the table of FIG. 8A.

FIG. 9A is a table identifying u', v' coordinates, CRI, R9, and melatonin suppressing milliwatts per 100 lumens values at a CCT of 5000K for a first reference point on the blackbody locus, a second reference point to the right of the blackbody locus, and a third reference point to the left of the blackbody locus.

FIG. 9B is a plot of the u', v' values for the three reference points identified in FIG. 9A superimposed on a 1976 CIE chromaticity diagram.

FIG. 10A is a first perspective view of a solid state emitter package that may embody one or more LED components as defined herein according to one embodiment, the emitter package including multiple LEDs arranged over an upper surface of a common substrate with multiple anodes and cathodes along a lower surface of the substrate.

FIG. 10B is a top plan view of a first subassembly of the emitter package of FIG. 10A, lacking a lens.

FIG. 10C is a top plan view of a second subassembly of the emitter package of FIG. 10A, lacking a lens, soldermask material, and LEDs.

FIG. 10D is a top plan view of a third subassembly of the emitter package of FIG. 10A, lacking a lens and LEDs.

FIG. 10E is a bottom plan view of each of the emitter package of FIG. 10A and the subassemblies of FIGS. 1B, 1C, and 1D.

FIG. 10F is a right side elevation view of the first subassembly of FIG. 10B.

FIG. 10G is a side cross-sectional view of the third subassembly of FIG. 10D, taken along section lines "A"-"A" depicted in FIG. 10E.

FIG. 10H is an exploded right side elevation view of the emitter package of FIG. 10A, separately depicting the lens registered with the first subassembly of FIG. 10B.

FIG. 10I is a second perspective view of the emitter package of FIG. 10A.

FIGS. 11A to 11H illustrate a top plan schematic views of light emitting apparatuses including first and second LED components according to various embodiments.

FIG. 12 is a simplified schematic diagram illustrating interconnections between various components of a light emitting apparatus including first and second LED components arranged in series and at least one control circuit.

FIG. 13 is a simplified schematic diagram illustrating interconnections between various components of a light emitting apparatus including first and second LED components arranged in parallel and at least one control circuit.

FIG. 14 is a simplified plan view of a light emitting apparatus including multiple LED components and at least one control circuit.

FIG. 15 is a simplified plan view of another light emitting apparatus including multiple LED components and at least one control circuit.

FIG. 16 is a perspective assembly view of a display device including direct backlight including a two-dimensional array of light emitting devices as described herein arranged to backlight a display (e.g., LCD) panel.

FIG. 17 is a perspective assembly view of a display device including a waveguide arranged to be lit along edges thereof by multiple light emitting devices as described herein, with the waveguide arranged to backlight a display (e.g., LCD) panel.

FIG. 18 is a schematic view of an array of light emitting devices as described herein arranged to be controlled with a control element.

DETAILED DESCRIPTION

Figure 11A:
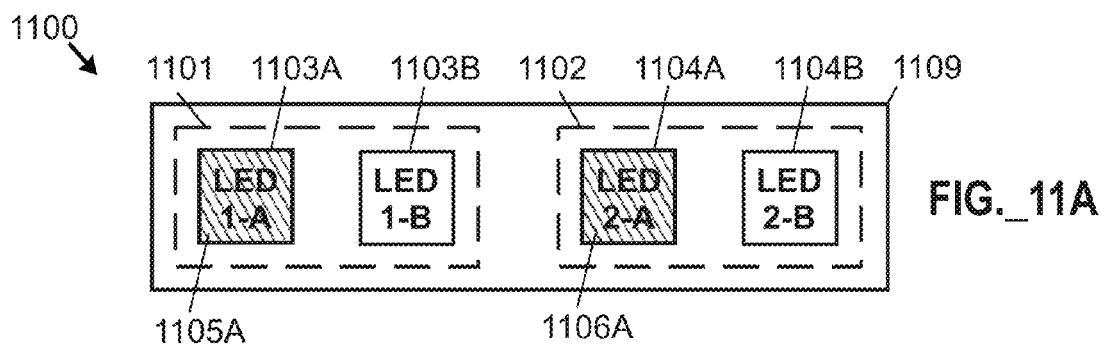

As noted previously, the art continues to seek improved lighting devices that address one or more limitations inherent to conventional devices. It would be desirable to permit adjustment of melatonin suppression characteristics of lighting devices (including, but not limited to, backlights) to ameliorate or reduce symptoms of circadian rhythm disorders or other health conditions, to avoid interference with sleep cycles, and/or to enhance nighttime worker alertness and performance. It would be desirable to provide one or more of the foregoing effects while maintaining high color rendering index values acceptably high for the intended use, or (in the case of backlights or other displays) to provide adjustable melatonin suppression effects while maximizing gamut of displayed images and therefore improve color vividness. It would also be desirable to provide lighting devices permitting adjustment of melatonin suppression characteristics without dramatically altering CCT. If would also be desirable to provide lighting devices permitting adjustment of color temperature and also permitting adjustment of melatonin suppression characteristics. It would further be desirable to provide lighting devices with high luminous efficacy and enhanced energy efficiency. It would also be desirable to provide lighting devices with reduced size, enhanced configuration flexibility, and/or extended duration of service.

The present invention relates in various aspects to solid state (e.g., LED) lighting devices including multiple solid state light emitting (e.g., LED) that are controllable to permit adjustment of melatonin suppression effects. In certain embodiments, a light emitting apparatus includes multiple LED components having substantially the same or similar chromaticity (e.g., each having a CCT within a specified number of MacAdam ellipses of a target CCT) but having melatonin suppression effects that differ by a predetermined threshold (e.g., at least about 5%, 10%, 15%, 20% 25%, 30%, 35%, 40%, 50%, 60%, 70%, 80%, 100%, 125%, 150%, 200%, 300%, 400%, or more) may be separately controlled separately, to permit aggregated melatonin suppression effects of the light emitting apparatus to be adjusted. In certain embodiments, a control circuit may be provided to permit switching between multiple predefined modes of operating a first LED component and a second LED component, wherein a first operating mode is arranged to generate combined emissions of the first and second LED components within a specified number of (e.g., preferably from one to six, more preferably four or fewer) MacAdam ellipses of a target CCT and having a first melatonin suppression milliwatt per hundred lumens value, and wherein a second operating mode is arranged to generate combined emissions of the first and second LED components within a specified number of (e.g., preferably from one to six, more preferably four or fewer) MacAdam ellipses of a target CCT and having a second melatonin suppression milliwatt per hundred lumens value that differs from the first melatonin suppression value by a predetermined threshold as described herein. In certain embodiments, a light emitting apparatus may provide adjustable CCT output, and further provide adjustable msm/100 l at different CCT values. In certain embodiments, a light emitting apparatus may comprise a backlight arranged to illuminate a display panel, the backlight including first and second LED components and a timer arranged to trigger switching between a first operating mode and a second operating mode, wherein each operating mode is arranged to generate combined emissions of the first and second LED components within a specified number of (e.g., preferably from one to six, more preferably four or fewer) MacAdam ellipses of a target CCT, but each operating mode provides a different melatonin suppression characteristic (e.g., wherein a second melatonin suppression milliwatt per hundred lumens value associated with a second operating mode differs from a first melatonin suppression milliwatt per hundred lumens value associated with a first operating mode by a predetermined threshold as described herein).

By providing multiple LED components having different melatonin suppressing effects (and preferably with similar chromaticities) in a single lighting device or apparatus, such components may be controlled to permit aggregated emissions to be adjusted for one or more desired effects. For example, if enhanced melatonin suppression effects are desired (e.g., in order to promote wakefulness or alertness), then a greater proportion of total power may be supplied to one or more individual LED component(s) having greater melatonin suppression effects relative to one or more other LED component(s) of the same device having lesser melatonin suppression effects. Conversely, if reduced melatonin suppression effects are desired (e.g., in order to reduce potential interference with a user's ability to fall asleep), then a greater proportion of total power may be supplied to one or more individual LED component(s) having lesser melatonin suppression effects relative to one or more other LED component(s) of the same device having greater melatonin suppression effects.

As noted previously, FIG. 1 includes six data points along the visible light portion of the melatonin action spectrum (a/k/a the melatonin affecting region). By integrating the amount of light (milliwatts) within the melatonin action spectrum and dividing such value by the number of photopic lumens, a relative measure of melatonin suppression effects of a particular light source can be obtained. A scaled relative measure denoted "melatonin suppressing milliwatts per hundred lumens" may be obtained by dividing the photopic lumens by 100. The term "melatonin suppressing milliwatts per hundred lumens" or the abbreviations "msm/100 I" or "Mel mW/100 lumens" consistent with the foregoing calculation method are used throughout this application and the accompanying figures. FIG. 4A is a table including values for the melatonin action spectrum (relative units) and corresponding wavelengths, while FIG. 4B is a line chart for melatonin action spectrum showing the values depicted in FIG. 4A.

FIG. 5 is a table including CCT, CRI, and msm/100 l values for various light sources. As shown in FIG. 5, an incandescent lamp provides a very high CRI value (~100) at full brightness, provides a relatively low msm/100 I value (~54) at such condition, but provides a much lower msm/100 I value (~25) when dimmed significantly. A Cree TrueWhite® LED CR6 (including a blue LED arranged to stimulate emission of a yellow phosphor in combination with a red LED) performs similarly to an incandescent lamp, providing a CRI value (~93) and msm/100 I value (~46) at full brightness, with a reduced msm/100 I value (~27) when dimmed significantly. Generally increasing msm/100 I values (provided in parentheses) are obtained from lighting apparatuses of the following types: metal halide (72), tri-phosphor fluorescent (66), standard fluorescent (80), Cree cool white EasyWhite® LED including a blue LED arranged to stimulate emissions of both yellow and red phosphors (90), sun on a white wall (120), daylight fluorescent (125), and blue sky (200). FIG. 6 is a plot of melatonin suppressing milliwatts per 100 lumens versus CCT obtained by modeling a solid state light source including a blue LED arranged to stimulate emissions of a yellow lumiphor in combination with a red LED, showing increasing milliwatts per 100 lumens with increasing CCT. As is apparent from FIGS. 5 and 6, msm/100 I values generally increase with increasing CCT—as to be expected, since increasing CCT corresponds to increased blue content, and the melatonin response spectrum has a peak value in the long wavelength portion (460-480) of the blue spectral range. Although FIG. 5 demonstrates that msm/100 I values may be altered by substituting light sources having different CCT values, individual light sources referenced in FIG. 5 are generally not capable of permitting adjustment of msm/100 I values at a substantially constant CCT value.

While providing acceptably high CRI values together with adjustable melatonin suppression effects may be desirable for general illumination, in other contexts (such as backlights for televisions, computer monitors, telephones, personal digital devices, table computers, and the like) it may be desirable to provide adjustable melatonin suppression effects while maximizing (or not unduly restricting) gamut of displayed images. In certain embodiments directed to backlights and backlighting, devices as disclosed herein may be adapted to output at least one gamut encompassing one or more of the following RGB color spaces: Adobe RGB, Apple RGB, CIE RGB, ColorMatch RGB, HDTV RGB (also known as sRGB), NTSC RGB, PAL/SECAM RGB, SGI RGB, SMPTE-C RGB, SMPTE-240M RGB, and Wide Gamut RGB. Such color spaces are well understood by those skilled in the art, and are described by Pascale, D., "A Review of RGB Color Spaces . . . from xyY to R'G'B'", available online at http://www.babelcolor.com/download/A%20review%20of%20RGB%20color%20spaces.pdf. (Such reference is hereby incorporated by reference herein.) In backlight applications, colors of LEDs and lumiphoric materials may generally include narrow band LEDs or phosphors in order to maximize gamut of the displayed images and improve color vividness. This is opposed to general illumination applications where LED and phosphor colors may preferably include at least one wide band phosphor (e.g., BSY type using BOSE, YAG, or LuAG) chosen to provide suitably high color rendering based on CRI.

Unless otherwise defined, terms used herein should be construed to have the same meaning as commonly understood by one of ordinary skill in the art to which this invention belongs. It will be further understood that terms used herein should be interpreted as having a meaning that is consistent with their meaning in the context of this specification and the relevant art, and should not be interpreted in an idealized or overly formal sense unless expressly so defined herein.

Embodiments of the invention are described herein with reference to cross-sectional, perspective, elevation, and/or plan view illustrations that are schematic illustrations of idealized embodiments of the invention. Variations from the shapes of the illustrations as a result, for example, of manufacturing techniques and/or tolerances, are to be expected, such that embodiments of the invention should not be construed as limited to particular shapes illustrated herein. This invention may be embodied in different forms and should not be construed as limited to the specific embodiments set forth herein. In the drawings, the size and relative sizes of layers and regions may be exaggerated for clarity.

Unless the absence of one or more elements is specifically recited, the terms "comprising," "including," and "having" as used herein should be interpreted as open-ended terms that do not preclude the presence of one or more elements.

It will be understood that when an element such as a layer, region, or substrate is referred to as being "on" another element, it can be directly on the other element or intervening elements may be present. Moreover, relative terms such as "on", "above", "upper", "top", "lower", or "bottom" are used herein to describe one structure's or portion's relationship to another structure or portion as illustrated in the figures. It will be understood that relative terms such as "on", "above", "upper", "top", "lower" or "bottom" are intended to encompass different orientations of the device in addition to the orientation depicted in the figures. For example, if the device in the figures is turned over, structure or portion described as "above" other structures or portions would now be oriented "below" the other structures or portions.

The terms "solid state light emitter" or "solid state emitter" may include a light emitting diode, laser diode, organic light emitting diode, and/or other semiconductor device which includes one or more semiconductor layers, which may include silicon, silicon carbide, gallium nitride and/or other semiconductor materials, a substrate which may include sapphire, silicon, silicon carbide and/or other microelectronic substrates, and one or more contact layers which may include metal and/or other conductive materials.

Solid state light emitting devices according to embodiments of the invention may include III-V nitride (e.g., gallium nitride) based LED chips or laser chips fabricated on a silicon, silicon carbide, sapphire, or III-V nitride growth substrate, including (for example) devices manufactured and sold by Cree, Inc. of Durham, N.C. Such LEDs and/or lasers may be configured to operate such that light emission occurs through the substrate in a so-called "flip chip" orientation. Such LED and/or laser chips may also be devoid of growth substrates (e.g., following growth substrate removal). LED chips useable with lighting devices as disclosed herein may include horizontal devices (with both electrical contacts on a same side of the LED) and/or vertical devices (with electrical contacts on opposite sides of the LED).

Solid state light emitters as disclosed herein may be used individually or in groups to emit one or more beams to stimulate emissions of one or more lumiphoric materials (e.g., phosphors, scintillators, lumiphoric inks, quantum dots, day glow tapes, etc.) to generate light at one or more peak wavelength, or of at least one desired perceived color (including combinations of colors that may be perceived as white). Inclusion of lumiphoric (also called 'luminescent') materials in lighting devices as described herein may be accomplished by direct coating on lumiphor support elements or lumiphor support surfaces (e.g., by powder coating, inkjet printing, or the like), adding such materials to lenses, and/or by embedding or dispersing such materials within lumiphor support elements or surfaces. Examples of lumiphoric materials are disclosed, for example, in U.S. Pat. No. 6,600,175 and U.S. Patent Application Publication No.

2009/0184616. Other materials, such as light scattering elements (e.g., particles) and/or index matching materials, may be associated with a lumiphoric material-containing element or surface. LED devices and methods as disclosed herein may include have multiple LEDs of different colors, one or more of which may be white emitting (e.g., including at least one LED with one or more lumiphoric materials). One or more luminescent materials useable in devices as described herein may be down-converting or up-converting, or can include a combination of both types.

The term "LED component" as used herein refers to one or more LEDs optionally arranged to stimulate emissions of one or more lumiphoric materials. According to certain embodiments, a single LED component may include multiple LEDs devoid of any lumiphor material, a single LED arranged to stimulate emissions of a single lumiphoric material, a single LED arranged to stimulate emissions of multiple lumiphoric materials, multiple LEDs arranged to stimulate emissions of a single lumiphoric material, multiple LEDs arranged to stimulate emissions of multiple lumiphoric materials, or a single LED arranged to stimulate emissions of one or more lumiphoric materials in combination with one or more additional LEDs not arranged to stimulate emissions of one or more lumiphoric materials. A LED component may include one or more lumiphoric materials located remotely from (e.g., spatially segregated from), but arranged to be stimulated by, one or more LEDs. (In certain embodiments, LEDs associated with multiple LED components may be arranged to stimulate one or more lumiphoric materials spatially segregated from LEDs associated with the multiple LED components.) When a LED component includes one or more lumiphoric materials arranged to be stimulated by at least one LED, emissions of at least one LED may be only partially absorbed by the one or more lumiphoric materials (wherein emissions output by the LED component include an unabsorbed portion of emissions of the at least one LED in combination with emissions of the one or more lumiphoric materials) according to certain embodiments, whereas in other embodiments substantially all emissions of at least one LED are absorbed by one or more lumiphoric materials (wherein emissions output by the LED component consist of emissions of the one or more lumiphoric materials). When a LED component includes multiple LEDs, such LEDs may be controlled as a group according to certain embodiments, whereas such LEDs may be separately controlled according to other embodiments.

In certain embodiments, control of one or more solid state emitter groups or sets may be responsive to a control signal (optionally including at least one sensor arranged to sense electrical, optical, and/or thermal properties and/or environmental conditions), a timer or clock signal, and/or at least one user input, and a control system may be configured to selectively provide one or more control signals to at least one current supply circuit. In various embodiments, current to different circuits or circuit portions may be pre-set, user-defined, or responsive to one or more inputs or other control parameters.

The term "substrate" as used herein in connection with lighting apparatuses refers to a mounting element on which, in which, or over which multiple solid state light emitters (e.g., emitter chips) may be arranged or supported (e.g., mounted). Exemplary substrates useful with lighting apparatuses as described herein include printed circuit boards (including but not limited to metal core printed circuit boards, flexible circuit boards, dielectric laminates, and the like) having electrical traces arranged on one or multiple surfaces thereof, support panels, and mounting elements of various materials and conformations arranged to receive, support, and/or conduct electrical power to solid state emitters. A unitary substrate may be used to support multiple LED components (e.g., multiple groups of solid state emitter components), and may further be used to support (and/or to be in electrical communication with) various circuit elements (e.g., control circuits, driver circuit elements, rectifier circuit elements, power supply elements, current limiting circuit elements, current diverting circuit elements, dimmer circuit elements, surge protection elements, electrostatic discharge elements, and the like), sensors, timers/clocks, and/or user input elements. In certain embodiments, a substrate may include multiple emitter mounting regions each arranged to receive one or more solid state light emitters and/or LED components. In certain embodiments, substrates may include conductive regions arranged to conduct power to solid state light emitters or solid state light emitter groups arranged thereon or there over. In other embodiments, substrates may be insulating in character, and electrical connections to solid state emitters may be provided by other means (e.g., via conductors not associated with substrates).

In certain embodiments, a substrate, mounting plate, or other support element on or over which multiple LED components may be mount may comprise one or more portions of, or all of, a printed circuit board (PCB), a metal core printed circuit board (MCPCB), a flexible printed circuit board, a dielectric laminate (e.g., FR-4 boards as known in the art) or any suitable substrate for mounting LED chips and/or LED packages. In certain embodiments, a substrate may comprise one or more materials arranged to provide desired electrical isolation and high thermal conductivity. In certain embodiments, at least a portion of a substrate may include a dielectric material to provide desired electrical isolation between electrical traces or components of multiple LED sets. In certain embodiments, a substrate can comprise ceramic such as alumina, aluminum nitride, silicon carbide, or a polymeric material such as polyimide, polyester, etc. In certain embodiments, substrate can comprise a flexible circuit board or a circuit board with plastically deformable portions to allow the substrate to take a non-planar (e.g., bent) or curved shape allowing for directional light emission with LED chips of one or more LED components also being arranged in a non-planar manner.

In certain embodiments, a substrate can be provided in a relatively small form factor in any desired shape (e.g., square, round, non-square, non-round, symmetrical and/or asymmetrical). Examples of small footprints or form factors of multi-emitter solid state light emitting apparatuses (e.g., including LED packages) including multiple LED component as described herein may include less than 5 cm$^2$, less than 3 cm$^2$, less than 2 cm$^2$, less than 1 cm$^2$, less than 0.5 cm$^2$, less than 0.3 cm$^2$, or less than 0.25 cm$^2$. LED chips of any suitable size or form factor may be included in a multi-emitter lighting emitting apparatus, including chips having a width of up to about 2000 microns, up to about 1000 microns, up to about 500 microns, up to about 350 microns, or any other suitable size. In other embodiments, a substrate may comprise a larger form factor, such as may be suitable for replacement of elongated fluorescent tube-type bulbs or replacement of relatively large light fixtures.

In certain embodiments, one or more LED components can include one or more "chip-on-board" (COB) LED chips and/or packaged LED chips that can be electrically coupled or connected in series or parallel with one another and mounted on a portion of a substrate. In certain embodiments, COB LED chips can be mounted directly on portions of substrate without the need for additional packaging. In certain embodiments, LED components may use packaged LED chips in place of COB LED chips. For example, in certain embodiments, LED components may utilize comprise serial or parallel arrangements of XLamp XM-L High-Voltage (HV) LED packages available from Cree, Inc. of Durham, N.C. Lighting devices as disclosed herein may include LED components including solid state emitters or groups of solid state emitters configured in various arrangements depending upon the application and/or voltage range desired. In certain embodiments, separately controllable solid stage emitters or groups of solid state emitters may be configured to operate at different voltages. Examples of possible operating voltages include, but are not limited to, 3V, 6V, and 12V.

In certain embodiments, one or more reflector elements (either symmetrical or asymmetrical in nature) may be attached to, integrally formed with, or otherwise associated with a substrate and arranged to reflect emissions from one or more (preferably multiple) LED components, such as to direct emissions in one or more desired directions and/or generate one or more desired beam patterns. In certain embodiments, one or more optical elements may be arranged to receive emissions from one or more (preferably multiple) LED components, and arranged to interact with such emissions to provide desired (e.g., light mixing, focusing, collimation, dispersion, and/or beam shaping) utility in either symmetrical or asymmetrical fashion. In certain embodiments, one or more optical elements may be provided in addition to one or more reflector elements.

In certain embodiments, lighting devices or light emitting apparatuses as described herein may include at least one LED with a peak wavelength in the visible range. In certain embodiments, one or more short wavelength solid state emitters (e.g., blue and/or cyan LED) may be used to stimulate emissions from at least one lumiphoric material, a mixture of lumiphoric materials, or discrete layers of lumiphoric material (e.g., including red, yellow, and green lumiphoric materials). In certain embodiments, at least two independently controlled short or medium wavelength (e.g., blue, cyan, or green) LEDs may be provided in a single LED component with at least one LED arranged to stimulate emissions of at least one lumiphors, which may comprise the same or different materials in the same or different amounts or concentrations relative to the LEDs. In certain embodiments, multiple electrically activated (e.g., solid state) emitters are provided, with groups of emitters being separately controllable relative to one another. In certain embodiments, one or more groups of solid state emitters as described herein may include at least a first LED chip comprising a first LED peak wavelength, and include at least a second LED chip comprising a second LED peak wavelength that differs from the first LED peak wavelength by at least 10 nm, by at least 20 nm, or by at least 30 nm (preferably, but not necessarily, in the visible range). In certain embodiments, solid state emitters with peak wavelengths in the ultraviolet (UV) range may be used to stimulate emissions of one or more wavelength conversion materials. Emitters having similar output wavelengths may be selected from targeted wavelength bins. Emitters having different output wavelengths may be selected from different wavelength bins, with peak wavelengths differing from one another by a desired threshold (e.g., at least 20 nm, at least 30 nm, at least 50 nm, or another desired threshold).

In certain embodiments, at least one LED component (and preferably multiple LED components) includes at least one solid state emitter arranged to stimulate at least one lumiphor, such as may be used to generate white or near-white light. In certain embodiments, one or more LED components may include one of one or more of the following items:

- a blue shifted yellow ("BSY") component including a principally blue solid state emitter (e.g., preferably including a peak wavelength in a range of from about 410 nm to about 480 nm, more preferably from about 455 nm to about 480 nm, still more preferably from about 465 nm to about 480 nm) arranged to stimulate emissions of a principally yellow lumiphor (e.g., preferably including a peak wavelength in a range of from 561 nm to 590 nm);
- a blue shifted (yellow plus red) ("BS(Y+R)") component including a principally blue solid state emitter arranged to stimulate emissions of a principally yellow lumiphor and a principally red lumiphor (e.g., preferably including a peak wavelength in a range of from about 591 nm to about 690 nm);
- a blue shifted red ("BSR") component including a principally blue solid state emitter arranged to stimulate emissions of a principally red lumiphor;
- a cyan shifted red ("CSY") component including a principally cyan solid state emitter (e.g., preferably including a peak wavelength in a range of from about 481 nm to about 505 nm) arranged to stimulate emissions of a principally yellow lumiphor;
- a cyan shifted red ("CSR") component including a principally cyan solid state emitter arranged to stimulate emissions of a principally red lumiphor;
- a green shifted red ("GSR") component including a principally green solid state emitter (e.g., including a peak wavelength in a range of from about 506 nm to about 560 nm) arranged to stimulate emissions of a principally red lumiphor;
- a UV shifted blue plus yellow ("UV(B+Y)") component including a principally ultraviolet solid state emitter (e.g., having a peak wavelength in the ultraviolet range, preferably shorter than about 400 nm) arranged to stimulate emissions of a principally blue lumiphor and a principally yellow lumiphor;
- a UV shifted blue plus red ("UV(B+R)") component including a principally ultraviolet solid state emitter arranged to stimulate emissions of a principally blue lumiphor and a principally red lumiphor;
- a UV shifted cyan plus yellow ("UV(C+Y)") component including a principally ultraviolet solid state emitter arranged to stimulate emissions of a principally cyan lumiphor and a principally yellow lumiphor;
- a UV shifted cyan plus red ("UV(C+R)") component including a principally ultraviolet solid state emitter arranged to stimulate emissions of a principally cyan lumiphor and a principally red lumiphor;
- a UV shifted green plus red ("UV(G+R)") component including a principally ultraviolet solid state emitter arranged to stimulate emissions of a principally green lumiphor and a principally red lumiphor;
- supplementation of any of the foregoing items with at least one supplemental electrically activated solid state emitter (e.g., LED), preferably having a peak wavelength in the visible range of any suitable color; and
- supplementation of any of the foregoing items with at least one additional lumiphor having a peak wavelength of any suitable color.

Although the inventive subject matter is not limited to use of the foregoing components, light emitting apparatuses including any suitable combination of first and second components independently selected from the foregoing items are contemplated.

In certain embodiments, at least one first LED component may include one or more (preferably multiple) solid state emitters arranged to stimulate at least one lumiphor, and such at least one first LED component may be arranged in a single device with at least one second component including multiple LEDs of different peak wavelengths and not arranged to stimulate any lumiphor. For example, the second LED component may include a RGB component, or red, green, and blue LEDs, or any other suitable combination of differently-colored LEDs that may be arranged to generate white or near-white light.

Since the melatonin response spectrum has a peak value in the long wavelength portion (460 to 480 nm subset) of the blue spectral range, close to the cyan range, in certain embodiments, at least one LED component includes at least one principally blue LED and/or at least one blue lumiphor having a peak wavelength preferably in a range of from about 455 nm to about 480 nm, more preferably in a range of from about 465 to about 480 nm. Given the proximity of cyan (generally spanning 481 nm to 505 nm) to the peak of the melatonin response spectrum, in certain embodiments, at least one LED component includes at least one principally cyan LED and/or at least one cyan lumiphor having a peak wavelength in a range of from about 481 nm to about 505 nm.

Addition of at least one supplemental (e.g., red) emitter may be useful to enhance warmth of BSY or white emissions and/or improve color rendering. In certain embodiments, separate electrically activated constituents of one or more LED components (e.g., BSY and red emitters) may be separately controlled, as may be useful to adjust color temperature and/or to maintain a desired color point as temperature increases, optionally in response to signals received from one or more temperature sensors. In various embodiments, separate electrically activated constituents (e.g., BSY and red constituents) may be controlled together in a single LED component, or may be placed in different LED components that are separately controlled. One or more supplemental solid state emitters and/or lumiphors of any suitable color (or peak wavelength) may be substituted for one or more red light-emitting components, or may be provided in addition to one or more red light-emitting components.

In certain embodiments, a solid state lighting device may include one or more groups or sets of BSY light emitting components supplemented with one or more supplemental emitters, such as long wavelength blue, cyan, green, yellow, amber, orange, red or any other desired colors. Presence of a cyan solid state emitter and/or a cyan lumiphor is particularly desirable in certain embodiments to permit adjustment or tuning of color temperature of one or more LED components of a light emitting apparatus, since the tie line for a cyan solid state emitter having a ~487 nm peak wavelength is substantially parallel to the blackbody locus for a color temperature of less than 3000K to about 4000K. (See, e.g., FIG. 2, wherein an imaginary line drawn from the 487 nm value at the left gamut boundary to the blackbody locus is substantially parallel to the BBL from ~3000K to ~4000K.) In certain embodiments, one or more constituents of a LED component may be controlled separately, such as may be useful to adjust intensity, permit tuning of output color, permit tuning of color temperature, and/or affect dissipation of heat generated by the light emitting components.

In certain embodiments, one or more LED components as described herein may include multiple independently controllable BSY emitters, optionally supplemented with one or more additional LEDs and/or lumiphors. In certain embodiments, multiple BSY emitters present in one or more components of a single lighting device (e.g., whether in the same or different components, optionally within one or more solid state emitter packages) may include blue LEDs with different peak wavelengths (e.g., LED peak wavelengths that differ from one another by one of the following wavelength thresholds: at least 5 nm, at least 10 nm, at least 15 nm, at least 20 nm, at least 25 nm, at least 30 nm, at least 35 nm, and at least 40 nm), and/or yellow lumiphors with different peak wavelengths (e.g., lumiphor peak wavelengths that differ from one another by one of the following wavelength thresholds: at least 5 nm, at least 10 nm, at least 15 nm, at least 20 nm, at least 25 nm, at least 30 nm, at least 35 nm, and at least 40 nm).

The expression "peak wavelength", as used herein, means (1) in the case of a solid state light emitter, to the peak wavelength of light that the solid state light emitter emits if it is illuminated, and (2) in the case of a lumiphoric material, the peak wavelength of light that the lumiphoric material emits if it is excited.

In certain embodiments, a first blue or shorter wavelength LED and a separately controllable second blue or shorter wavelength LED may both be arranged to stimulate emissions of a remote lumiphor (e.g., including a yellow lumiphor such as may include a YAG phosphor) spatially separated from both LEDs, and combined with a red emitting LED. Peak wavelengths of the first LED and second LED may differ from one another by preferably at least about 20 nm, at least about 25 nm, at least about 30 nm, at least about 35 nm, at least about 40 nm, at least about 45 nm, or at least about 50 nm. For example, a first LED may include a relatively longer (blue) peak wavelength (e.g., preferably from about 430 nm to about 470 nm, more preferably from about 440 nm to about 460 nm, more preferably from about 445 nm to about 455 nm, more preferably about 450 nm) and the second LED may include a relatively shorter (blue or near UV) peak wavelength (e.g., preferably from about 390 nm to about 425 nm, more preferably from about 395 nm to about 420 nm, more preferably from about 400 nm to about 415 nm, more preferably from about 400 to about 410 nm). If a first LED is a longer wavelength blue (e.g., peak wavelength ~450 nm) the second LED is a shorter wavelength blue or near UV (e.g., peak wavelength ~410 nm), the first and second LEDs are independently controllable and arranged to stimulate emissions of a yellow YAG phosphor (and combined with a red LED) in order to generate warm white light having a CCT of around 2700K, then the msm/100 I value for the resulting combination is expected to be ~40 msm/100 I when the first LED is operated, whereas the msm/100 I value for the resulting combination is expected to be ~100 msm/100 I. The resulting difference in melatonin suppression effects from a value of 40 msm/100 I to 100 msm/100 I represents an increase of about 150%. In another embodiment, if an even shorter wavelength (e.g., ~400 nm peak wavelength) second LED is substituted for the 410 nm peak wavelength in the foregoing device, then the resulting combination is expected to output light having a msm/100 I value of about 200 msm/100 I at a CCT of 2700. The resulting difference in melatonin suppression effects from a value of about 40 msm/100 I to about 200 msm/100 I represents an increase of about 400%. This demonstrates that selection and independent operation of LEDs with different peak wavelengths may be used to significantly affect melatonin suppression effects of a lighting device.

In certain embodiments, light emitting apparatuses as disclosed herein may be used as described in U.S. Pat. No. 7,213,940, which is hereby incorporated by reference. In certain embodiments, a combination of light (aggregated emissions) exiting a lighting emitting apparatus including multiple LED components as disclosed herein, may, in an absence of any additional light, produce a mixture of light having x, y color coordinates within an area on a 1931 CIE Chromaticity Diagram defined by points having coordinates (0.32, 0.40), (0.36, 0.48), (0.43, 0.45), (0.42, 0.42), (0.36, 0.38). In certain embodiments, combined emissions from a lighting emitting apparatus as disclosed herein may embody at least one of (a) a color rendering index (CRI Ra) value of at least 85, and (b) a color quality scale (CQS) value of at least 85.

Some embodiments of the present invention may use solid state emitters, emitter packages, fixtures, luminescent materials/elements, power supply elements, control elements, and/or methods such as described in U.S. Pat. Nos. 7,564, 180; 7,456,499; 7,213,940; 7,095,056; 6,958,497; 6,853, 010; 6,791,119; 6,600,175, 6,201,262; 6,187,606; 6,120, 600; 5,912,477; 5,739,554; 5,631,190; 5,604,135; 5,523, 589; 5,416,342; 5,393,993; 5,359,345; 5,338,944; 5,210, 051; 5,027,168; 5,027,168; 4,966,862, and/or 4,918,497, and U.S. Patent Application Publication Nos. 2009/ 0184616; 2009/0080185; 2009/0050908; 2009/0050907; 2008/0308825; 2008/0198112; 2008/0179611, 2008/ 0173884, 2008/0121921; 2008/0012036; 2007/0253209; 2007/0223219; 2007/0170447; 2007/0158668; 2007/ 0139923, and/or 2006/0221272; with the disclosures of the foregoing patents and published patent applications being hereby incorporated by reference as if set forth fully herein.

The expressions "lighting device" and "light emitting apparatus", as used herein, are not limited, except that they are capable of emitting light. That is, a lighting device or light emitting apparatus can be a device which illuminates an area or volume, e.g., a structure, a swimming pool or spa, a room, a warehouse, an indicator, a road, a parking lot, a vehicle, signage, e.g., road signs, a billboard, a ship, a toy, a mirror, a vessel, an electronic device, a boat, an aircraft, a stadium, a computer, a remote audio device, a remote video device, a cell phone, a tree, a window, an LCD display, a cave, a tunnel, a yard, a lamppost, or a device or array of devices that illuminate an enclosure, or a device that is used for edge or back-lighting (e.g., backlight poster, signage, LCD displays), light bulbs, bulb replacements (e.g., for replacing AC incandescent lights, low voltage lights, fluorescent lights, etc.), outdoor lighting, security lighting, exterior residential lighting (wall mounts, post/column mounts), ceiling fixtures/wall sconces, under cabinet lighting, lamps (floor and/or table and/or desk), landscape lighting, track lighting, task lighting, specialty lighting, ceiling fan lighting, archival/art display lighting, high vibration/impact lighting-work lights, etc., mirrors/vanity lighting, or any other light emitting devices. In certain embodiments, lighting devices or light emitting apparatuses as disclosed herein may be self-ballasted.

The inventive subject matter further relates in certain embodiments to an illuminated enclosure (the volume of which can be illuminated uniformly or non-uniformly), comprising an enclosed space and at least one lighting device or light emitting apparatus as disclosed herein, wherein at least one lighting device or light emitting apparatus illuminates at least a portion of the enclosure (uniformly or non-uniformly). The inventive subject matter further relates to an illuminated area, comprising at least one item, e.g., selected from among the group consisting of a structure, a swimming pool or spa, a room, a warehouse, an indicator, a road, a parking lot, a vehicle, signage, e.g., road signs, a billboard, a ship, a toy, a mirror, a vessel, an electronic device, a boat, an aircraft, a stadium, a computer, a remote audio device, a remote video device, a cell phone, a tree, a window, a LCD display, a cave, a tunnel, a yard, a lamppost, etc., having mounted therein or thereon at least one lighting device or light emitting apparatus as described herein. Methods include illuminating an object, a space, or an environment, utilizing one or more lighting devices or light emitting apparatuses as disclosed herein.

In certain embodiments, a lighting apparatus includes multiple LED components having different melatonin suppression effects, but preferably having similar chromaticities (e.g., within a specified number (e.g., preferably seven or fewer, more preferably four or fewer, more preferably three or fewer, or two or fewer) MacAdam ellipses of a target CCT), are arranged on a common substrate or mounting plate, and are subject to being controlled by one or more control circuits. In certain embodiments, a lighting apparatus includes multiple LED components, wherein combined emissions of the multiple components are at or near (e.g., within a number of MacAdam ellipses as specified herein) a target correlated color temperature in a range of from about 2000K to 8000K, more preferably in a range of from about 2500K to 6000K. In certain embodiments, each LED component is separately arranged to output emissions at or near (e.g., within a number of MacAdam ellipses as specified herein) a target correlated color temperature in a range of from about 2000K to 8000K, more preferably in a range of from about 2500K to 6000K.

In certain embodiments, a lighting apparatus as disclosed herein includes multiple LED components arranged in an array (e.g., a two-dimensional array). In certain embodiments, emitters of a first LED component may be interspersed with emitters of a separately controllable second LED component (e.g., with emitters of a first LED component arranged in a two-dimensional array that is superimposed with emitters of a second LED component arranged in a two dimensional array), such as may be beneficial to promote color mixing, optionally aided with one or more diffuser elements.

In certain embodiments, individual emitters within a multi-emitter LED component may be arranged in series, in parallel, or in a series-parallel relationship. In certain embodiments, multiple LED components of a solid state light emitting apparatus may be arranged in series, in parallel, or in series-parallel relationship. In certain embodiments, a light emitting apparatus as described herein may include at least one control circuit arranged to independently supply current (or adjust relative supply of current) to at least one of the first LED component and the second LED component to operate (e.g., simultaneously) the first LED component and the second LED component according to the first operating mode or the second operating mode (and optionally according to third, fourth, and/or additional operating modes). In certain embodiments, modulation of current and/or duty cycle may be performed with one or more current bypass and/or current shunt elements that may be optionally controlled by one or more control circuits.

In certain embodiments, at least one control circuit arranged to control one or more LED components may include a current supply circuit configured to independently apply an on-state drive current to each individual solid state emitter or each individual LED component. In certain embodiments, drive currents may be pulsed, such as with pulse width modulation. Control of one or more solid state emitters may be responsive to a control signal (optionally including at least one sensor arranged to sense electrical, optical, and/or thermal properties and/or environmental conditions), and a control system may be configured to selectively provide one or more control signals to at least one current supply circuit. In various embodiments, current to different circuits or circuit portions may be pre-set, user-defined, or responsive to one or more inputs or other control parameters.

In certain embodiments, one or more control circuit elements may be operated or controlled responsive to one or more user input elements, one or more timer or clock elements, and/or one or more sensor elements (e.g., temperature sensing element, photosensors, etc.). One or more input elements, timer or clock elements, and/or sensors may be used to trigger switching between at least first and second modes of a light emitting apparatus as described herein. Multiple elements of the preceding group may be provided. In certain embodiments, one or more control circuit elements, user input elements, timer or clock elements, and/or sensor elements may be supported by and/or in electrical communication with a substrate of a lighting apparatus. In certain embodiments, a photosensor may be arranged to receive ambient light, while being shielded or otherwise placed to prevent receipt of direct light emissions from a first LED component and a second LED component. In certain embodiments, a photosensor may be used to trigger switching between operating modes of a light emitting apparatus as described herein, such as by adjusting current and/or duty cycle of different LED components responsive to presence, absence, or level of ambient light, or responsive to presence or absence of motion (e.g., as indicative of presence or absence of a person, a vehicle, or another object).

In certain embodiments, a user input element arranged to receive a user input may be in wired or wireless communication with a light emitting apparatus. In certain embodiments, a user input element, timer/clock, sensing element, and/or control circuit may include a dedicated or general purpose computer, or a dedicated or general purpose personal electronic device, arranged to implement software or other machine readable instructions to implement desired input and/or control functionality for use with a light emitting apparatus as disclosed herein. In certain embodiments, a memory or other data logging element or apparatus may be associated with a light emitting apparatus as disclosed herein and arranged to receive and store information indicative of binning, performance specifications, operating characteristics, operating parameters, operating time, calibration parameters, maintenance requirements, or other information relating to production, calibration, operation, maintenance, and/or servicing.

In certain embodiments, a light emitting apparatus may include a first LED component and a second LED component, wherein the first LED component and the second LED component are arranged to be operated in a first operating mode in which combined emissions of the first LED component and the second LED component (i) are within four MacAdam ellipses of a target correlated color temperature, and (ii) embody a first melatonin suppression milliwatt per hundred lumens value, and wherein the first LED component and the second LED component are arranged to be operated in a second operating mode in which combined emissions of the first LED component and the second LED component (i) are within four MacAdam ellipses of the target correlated color temperature, and (ii) embody a second melatonin suppression per hundred lumens value that is preferably at least about 10 percent greater (more preferably at least about 20 percent, at least about 30 percent, at least about 40 percent, or at least about 50 percent greater) than the first melatonin suppression per hundred lumens value. Combined emissions of a light emitting apparatus when operated in the first operating mode preferably embodies a color rendering index (CRI) value of at least about 80 (more preferably a value of at least about 85, still more preferably a value of at least about 90). Given the relatively narrow wavelength (e.g., full-width half-max) output of most electrically activated solid state emitters (including LEDs), it may be challenging to obtain high CRI values of 80 or more without use of lumiphoric materials unless a large number of electrically activated emitters having different peak wavelengths are used—but such an arrangement may be prohibitively expensive or impractical due to packaging constraints and/or color mixing issues. Accordingly, in light emitting apparatuses according to certain embodiments, at least one of the first LED component and the second LED component preferably includes at least one LED arranged to stimulate emissions of at least one lumiphoric material. In certain embodiments, a first LED component includes at least one first LED arranged to stimulate emissions of at least one first lumiphoric material, and a second LED component includes at least one second LED arranged to stimulate emissions of at least one second lumiphoric material.

As noted previously, combined emissions of a light emitting apparatus when operated in a first operating mode preferably embodies a color rendering index (CRI) value of at least about 80 (more preferably a value of at least about 85, still more preferably a value of at least about 90). When such a light emitting apparatus is operated in a second operating mode having increased emissions in the melatonin response spectrum (thereby providing increasing msm/100 l values), the fraction of emissions in blue and/or cyan spectrum will increase relative to colors characterized by longer wavelengths (e.g., green, yellow, red); accordingly, color rendering will typically decline. In certain embodiments, combined emissions of the first LED component and the second LED component when operated in the first operating mode embody a CRI value of preferably at least about 30 (more preferably at least about 40, more preferably at least about 50, still more preferably at least about 60). Although CRI values as low as 30 may not be pleasing for general illumination, such values may be acceptable for certain applications, such as backlighting of (e.g., LCD) displays.

In certain embodiments, a light emitting apparatus as described herein may include at least one control circuit arranged to adjust supply of current to at least one of the first LED component and the second LED component to operate the first LED component and the second LED component according to the first operating mode or the second operating mode.

In certain embodiments, one or more LED components of a light emitting apparatus as described herein may embody or be arranged in at least one solid state emitter package.

A solid state emitter package may include at least one solid state emitter chip (more preferably multiple solid state emitter chips) that is enclosed with packaging elements to provide environmental protection, mechanical protection, color selection, and/or light focusing utility, as well as electrical leads, contacts, and/or traces enabling electrical connection to an external circuit. One or more emitter chips may be arranged to stimulate one or more lumiphoric materials, which may be coated on, arranged over, or otherwise disposed in light receiving relationship to one or more solid state emitters. A lens and/or encapsulant materials, optionally including lumiphoric material, may be disposed over solid state emitters, lumiphoric materials, and/or lumiphor-containing layers in a solid state emitter package. Multiple solid state emitters may be provided in a single package. In certain embodiments, multiple LED components as described herein may be provided in a single package. In other embodiments, one or more LED components as described herein may include one or more LED packages. In certain embodiments, LED components are separately controllable. In certain embodiments, multiple LEDs within a LED component may be controlled independently of one another.

In certain embodiments, a package including multiple solid state emitters may include multiple die attach pads, with a single die attach pad supporting each separately controllable solid state emitter or each separately controllable group of solid state emitters. A package including multiple solid state emitters may include a single lens (e.g., a molded lens) arranged to transmit at least a portion of light emanating from each solid state emitter. In certain embodiments, a molded lens may be arranged in direct contact with LED chips, die attach pads, other electrical elements, and/or exposed insulating material along a top surface of a substrate comprising insulating material. In certain embodiments, a lens may be textured or faceted to improve light extraction, and/or a lens may contain or have coated thereon various materials such as lumiphors and/or scattering particles.

In certain embodiments, a light emitting apparatus including a first LED component and a second LED component as disclosed herein may include or be embodied in one or more LED packages. One or more LED packages may include one or more of the following features: a single leadframe arranged to conduct electrical power to the first LED component and the second LED component; a single reflector arranged to reflect at least a portion of light emanating from each of the first LED component and the second LED component; a single submount supporting the first LED component and the second LED component; a single lens (e.g., a molded lens) arranged to transmit at least a portion of light emanating from each of the first LED component and the second LED component; and a single diffuser arranged to diffuse at least a portion of light emanating from each of the first LED component and the second LED component.

In certain embodiments, a light emitting apparatus as disclosed herein (whether or not including one or more LED packages) may include at least one of the following items arranged to receive light from multiple LED components: a single lens; a single optical element; a single diffuser; and a single reflector. In certain embodiments, a light emitting apparatus including multiple LED components may include at least one of the following items arranged to receive light from multiple LED components: multiple lenses; multiple optical elements; and multiple reflectors. Examples of optical elements include, but are not limited to elements arranged to affect light mixing, focusing, collimation, dispersion, and/or beam shaping.

In certain embodiments, a light emitting apparatus including first and second LED components may provide adjustable CCT output, and further provide adjustable msm/100 l at different CCT values. For example, a first and a second operating mode may correspond to a first target CCT, and a third and a fourth operating mode may correspond to a second target CCT, wherein the second CCT differs from the first CCT by at least about 300K, at least about 600K, at least about 1000K, or any suitable value. The first and second operating modes provide msm/100 l values that differ from one another, and the third and fourth operating modes provide msm/100 l values that differ from one another. Such msm/100 l values differences are preferably at least about 10%, at least about 20%, at least about 30%, at least about 40%, at least about 50%, at least about 60%, at least about 80%, at least about 100%, at least about 125%, at least about 150%, at least about 200%, at least about 300%, at least about 400% or any other suitable difference threshold.

If a LED component includes multiple electrically activated solid state emitters (e.g., LEDs), then by adjusting operation of different electrically activated solid state emitters within the LED component, CCT output by the LED component may be altered. As noted previously, providing a cyan emitter (whether a cyan LED or a LED combined with a cyan lumiphor) in a LED component together with another electrically activated solid state emitter may beneficially permit color temperature to be varied over a color temperature range of less than 3000K to about 4000K, since the tie line for a cyan solid state emitter having a ~487 nm peak wavelength is substantially parallel to the blackbody locus for a color temperature of less than 3000K to about 4000K. Accordingly, with appropriate selection of supplemental emitters for use in a multi-emitter LED component, it is straightforward to adjust CCT of the LED component. When using first and second multi-emitter LED components, each LED component may have adjustable CCT, but when both LED components are arranged to operate at a common CCT value, a msm/100 l value of their combined emissions may be adjusted by adjusting total current supplied to the first LED component relative to the second LED component. In this manner, a light emitting apparatus may provide adjustable CCT output, and further provide adjustable msm/100 l at different CCT values.

In one embodiment, a first LED component and a second LED component are arranged to be operated at or near a first target correlated color temperature in a first operating mode in which combined emissions of the first LED component and the second LED component (i) are within four MacAdam ellipses of the first target correlated color temperature, and (ii) embody a first melatonin suppression milliwatt per hundred lumens value; wherein the first LED component and the second LED component are arranged to be operated at or near the first target correlated color temperature in a second operating mode in which combined emissions of the first LED component and the second LED component (i) are within four MacAdam ellipses of the first target correlated color temperature, and (ii) embody a second melatonin suppression per hundred lumens value that is at least about 10 percent greater than the first melatonin suppression per hundred lumens value; wherein the first LED component and the second LED component are arranged to be operated at or near a second target correlated color temperature in a third operating mode in which combined emissions of the first LED component and the second LED component (i) are within four MacAdam ellipses of the second target correlated color temperature, and (ii) embody a third melatonin suppression milliwatt per hundred lumens value; wherein the first LED component and the second LED component are arranged to be operated at or near the second target correlated color temperature in a fourth operating mode in which combined emissions of the first LED component and the second LED component (i) are within four MacAdam ellipses of the second target correlated color temperature, and (ii) embody a fourth melatonin suppression per hundred lumens value that is at least about 10 percent greater than the third melatonin suppression per hundred lumens value; and wherein the second target correlated color temperature differs from the first correlated color temperature preferably by at least about 300K (more preferably by at least about 600K, still more preferably by at least about 1000K). Preferably, each of the first LED component and the second LED component in such embodiment includes multiple electrically activated emitters (e.g., LEDs), optionally arranged to stimulate at least one lumiphoric material.

In certain embodiments, combined emissions of the first LED component and the second LED component when operated in at least one of the first operating mode and the third operating mode (or when operated in each of the first and second operating modes, at different times) embody a color rendering index (CRI) value of at least about 80. In such embodiments, combined emissions of the first LED component and the second LED component when operated in at least one of the second operating mode and the fourth operating mode (or whether operated in each of the second and fourth operating modes, at different times) may embody a color rendering index (CRI) value of at least about 30.

As noted previously, providing multiple LED components having different melatonin suppression characteristics in a single lighting device or apparatus wherein the LED may be separately controlled permits aggregated melatonin suppression characteristics of a lighting device to be adjusted. In certain embodiments, adjustment of melatonin suppression characteristics may be accompanied by small or minimal change in corrected color temperature (e.g., each having a CCT within a specified number of MacAdam ellipses of a target CCT as disclosed herein). In certain embodiments, a light emitting apparatus may provide adjustable CCT output, and further provide adjustable msm/100 I at different CCT values.

In certain embodiments, a backlight is arranged to illuminate a display panel arranged to display at least one of images and text, wherein the backlight includes a first LED component; a second LED component; and a timer or clock arranged to trigger switching between a first operating mode and a second operating mode; wherein in the first operating mode the first LED component and second LED component generate combined emissions that (i) are within four MacAdam ellipses of a target correlated color temperature, and (ii) embody a first msm/100 I value; and wherein in the second operating mode the first LED component and second LED component generate combined emissions that (i) are within four MacAdam ellipses of the target correlated color temperature, and (ii) embody a second msm/100 l value that is at least about 10 percent greater than the first msm/100 l value.

One advantage of providing a backlight having an associated timer (e.g., a user-adjustable timer apparatus) or clock arranged to trigger switching between operating modes having different msm/100 l values is that it permits a user to define a time period for maintaining a desired melatonin suppressing effect. For example, a user of an electronic reader or tablet computer may desire to read for a specified period (e.g., one hour) before sleeping but the user does not wish to remain awake substantially longer than the specified period. Such a user might set a timer associated with a backlight of the electronic reader or tablet computer to maintain a high msm/100 I value according to one operating mode for a defined period, such that at the end of the predefined period the timer will trigger the backlight to operate according to another operating mode having a reduced msm/100 I value to permit the user to start releasing melatonin and thereby permit the user to fall asleep.

Various illustrative features are described below in connection with the accompanying figures.

FIG. 7A is a table identifying lumens, total lumens, relative lumens, CRI, and msm/100 I versus CRI at a CCT of 3000K obtained by modeling combined output of a first LED component including a blue LED arranged to stimulate emissions of a yellow phosphor (i.e., a BSY component) and a second LED component including a cyan LED arranged to stimulate emissions of a red phosphor (i.e., a CSR component). FIG. 7B is plot of msm/100 I versus CRI at a CCT of 3000K using data listed in the table of FIG. 7A. As shown in FIGS. 7A-7B, maximum msm/100 I values are obtained by operating the second LED component exclusively while zero lumens are output by the first LED component, but the CRI value is extremely low (−22.6). As a greater proportion of lumens are output by the first (BSY) component, CRI values steadily improve (to an ultimate value of 94.1), but msm/100 I values decline (to an ultimate value of 51).

For purposes of general illumination typically requiring CRI of at least about 80, the potential operating modes depicted in the last three rows of FIG. 7A all provide CRI values exceeding 80, and with msm/100 1 values ranging from 51 to 56 (representing an increase of 9.8 percent going from a msm/100 l value of 51 to 56). This demonstrates that a roughly 10% increase in msm/100 1 can be obtained by operating two LED components (e.g., BSY and CSR components) according to different modes at a constant CCT of 3000K while maintaining CRI above 80.

For other purposes where color rendering may not be as critical (e.g., backlighting), comparison of the fourth and last lines of FIG. 7A demonstrates that msm/100 1 may be increased from a value of 51 (with a CRI value of 94.1) to a value of 72.4 (with a CRI value of 35.1). This demonstrates that a roughly 42% increase in msm/100 I can be obtained by operating two LED components (i.e., the specified BSY and CSR components) according to different operating modes at a constant CCT of 3000K while maintaining CRI above 30.

FIG. 8A is a table identifying lumens, total lumens, relative lumens, CRI, and msm/100 I versus CRI at a CCT of 5000K obtained by modeling combined output of a first LED component including a blue LED arranged to stimulate emissions of a yellow phosphor (i.e., a BSY component) and a second LED component including a cyan LED arranged to stimulate emissions of a red phosphor (i.e., a CSR component). FIG. 8B is plot of msm/100 I versus CRI at a CCT of 3000K using data listed in the table of FIG. 8A. As shown in FIGS. 8A-8B, the maximum msm/100 I value (140.3) is obtained by operating the second LED component exclusively while zero lumens are output by the first LED component, but the CRI value is extremely low (−44.5). As a greater proportion of lumens are output by the first (BSY) component, CRI values steadily improve (to an ultimate value of 95.7), but msm/100 I values decline (to an ultimate value of 90.7).

For purposes of general illumination typically requiring CRI of at least about 80, the potential operating modes depicted in the last three rows of FIG. 8A all provide CRI values exceeding 80, and with msm/100 I values ranging from 90.7 to 96 (representing an increase of 5.8 percent going from a msm/100 I value of 90.7 to 96). This demonstrates that a roughly 6% increase in msm/100 I can be obtained by operating two LED components (e.g., BSY and CSR components) according to different modes at a constant CCT of 5000K while maintaining CRI above 80.

For other purposes where color rendering may not be as critical (e.g., backlighting), comparison of the fourth and last lines of FIG. 8A demonstrates that msm/100 1 may be increased from a value of 90.7 (with a CRI value of 95.7) to a value of 110.1 (with a CRI value of 40.2). This demonstrates that a roughly 34% increase in msm/100 I can be obtained by operating two LED components (i.e., the specified BSY and CSR components) according to different operating modes at a constant CCT of 5000K while maintaining CRI above 30.

FIG. 9A is a table identifying u', v' coordinates, CRI, R9, and melatonin suppressing milliwatts per 100 lumens values at a CCT of 5000K for a first reference point on the blackbody locus, a second reference point to the right of the blackbody locus, and a third reference point to the left of the blackbody locus. FIG. 9B is a plot of the u', v' values for the three reference points identified in FIG. 9A superimposed on a 1976 CIE chromaticity diagram. The second and third reference points shown in FIG. 9B represent potential operating points of two separate LED components. If such LED components were provided in a single light emitting apparatus, then proportion of electric current may be adjusted to the components to provide a combined output embodying any point along an imaginary line from the second reference point (through the first reference point) to the third reference point. As shown in FIG. 9A, the second (right) reference point embodies a CRI of 79 and a msm/100 I value of 106.1, whereas the third (left) reference point embodies a CRI of 71 and a msm/100 I value of 93.5, and the first reference point embodies a CRI of 79 and a msm/100 I value of 106.1. Although FIGS. 9A-9B depict reference points at a CCT of 5000K, similar relationships are expected for combinations of emitters arranged to be operated at other CCT values.

As noted previously, in different embodiments, individual LED components of a solid state emitter apparatus may be arranged on different substrates, or multiple LED components may be arranged in or on a single substrate. In certain embodiments, multiple LED components as described herein may be arranged in a single solid state emitter package.

FIG. 10A illustrates a solid state emitter package 100 that may embody or include one or more LED components as described herein. The emitter package 100 includes multiple (e.g., four) LED chips 150A-150D that may be separately controlled and that are supported by an insulating substrate 110 (e.g., preferably, but not necessarily, comprising ceramic material) having an upper surface 111, a lower surface 112, and side walls 113-116 extending between the upper surface 111 and the lower surface 112. Electrical traces 140 are arranged over the substrate 110, including multiple die attach pads 141A-141D and additional electrical elements 142A-142D arranged proximate to the die attach pads 141A-141D. Where the die attach pads 141A-141D are electrically conductive, the LED chips 150A-150D may be arranged with bottom side contacts thereof in electrical communication with the die attach pads 141A-141D, and with top side contacts thereof in electrical communication with the electrical elements 142A-142D by way of wirebonds 152. The die attach pads 141A-141D and electrical elements 142A-142D may comprise one or more metals patterned on (or in) the top surface 111 of the substrate 110. Gaps 145 may be provided between adjacent die attach pads 141A-141D and/or electrical elements 142A-142D to prevent undesired conductive electrical communication. In certain embodiments, die attach pads need not be electrically conductive, such as in cases where anode and cathode connections to a solid state emitter chip are both made with wirebonds. Optional elements that may be formed concurrently with the electrical traces 140 but not serve as part of any conductive path through the package 100 include a polarity or positional identifying mark 148 and chip singulation alignment marks 149-1, 149-2 (used during singulation, such as by sawing, of emitter packages or subassemblies thereof from a wafer or superassembly from which multiple emitter packages are formed). An insulating soldermask 147 (shown in greater detail in FIG. 10B) is patterned over peripheral portions of the electrical traces 140, and a molded lens 160 (e.g., including a raised or hemispherical portion 161 and a base portion 162) is arranged over the top surface 111 of the substrate 110 and is arranged to transmit at least a portion of light generated by the emitter chips 150A-150D.

LED chips 150A-150D of any suitable peak wavelength (e.g., color) may be used, and optionally arranged to stimulate emissions of one or more lumiphors (e.g., phosphors). Although the LED chips 150A-150D may be separately controlled, in certain embodiments groups of two or more LED chips 150A-150D or groups of LED chips may be controlled together in a groupwise fashion. As noted previously, the package 100 may embody one or more LED components, with each LED component comprising at least one LED chip 150A-150D (optionally multiple LED chips), with one or more LED chips 150A-150D optionally arranged to stimulate emissions of one or more lumiphoric materials. In certain embodiments, the solid state emitter package 100 may include two LED components, with each LED component including two LED chips 150A-150D. In certain embodiments, the solid state emitter package 100 may include one, two, three, or four LED components. Although four LED chips 150A-150D are illustrated in FIG. 10A, it is to be appreciated that a LED package may include any desirable number of LED chips, including groups of chips arranged in series, in parallel, or in series-parallel configurations.

FIG. 10B is a top plan view of a first subassembly 100-3 of the emitter package 100 illustrated in FIG. 10A, with the subassembly 100-3 lacking the lens 160 and representing the solder mask 147 with hatched lines for emphasis. As shown in FIG. 10B, the solder mask 147 is arranged over peripheral portions of the top side electrical traces 140 between the substrate edges 113-116 and a roughly circular window arranged below a raised portion 161 of the lens 160.

FIG. 10C is a top plan view of a second subassembly 100-1 of the emitter package 100 illustrated in FIG. 10A, with the subassembly 100-1 lacking a lens, solder mask, and LEDs, but with the traces 140 represented with hatched lines for emphasis. As shown in FIG. 10C, the electrical traces 140 extend peripherally outward beyond the roughly circular window defined in the solider mask 147 (illustrated in FIG. 10B), with optional alignment holes 143A-143D defined in peripheral portions of the die attach pads 141A-141D, and optional alignment holes 144A-144D defined in peripheral portions of the additional electrical elements 142A-142D. The various alignment holes 143A-143D, 144A-144D may be used during manufacture, for example, to promote alignment with electrically conductive vias (e.g., as shown in FIG. 10G) defined through the insulating substrate 110.

FIG. 10D is a top plan view of a third subassembly 100-2 of the emitter package 100 illustrated in FIG. 10A, with the subassembly 100-2 lacking a lens, and LEDs, but with the solder mask 147 represented with hatched lines for emphasis FIG. 10E is a bottom plan view of each of the emitter package 100 of FIG. 10A and the subassemblies of FIGS. 1B, 1C, and 1D. A bottom surface 112 of the substrate includes four anodes 121A-121D and four cathodes 122A-122D patterned thereon (e.g., as electrical traces), with one paired anode/cathode per quadrant. The separate anodes 121A-121D and cathodes 122A-122D enable separate control of the multiple LED chips 150A-150B if desired. Each anode 121A-121D may include an optional alignment hole 123A-123D and each cathode 122A-122D may include an optional alignment hole 124A-124D. The various anodes 121A-121D and cathodes 122A-122D are separated by gaps that may be filled with solder mask material sections 127-1, 127-2. A thermal element (e.g., thermal spreading element) 126 may be arranged along the bottom surface 112 between the solder mask material sections 127-1, 127-2 and generally underlapping the solid state emitters 150A-150D. The thickness of the thermal element 126 may be the same as or different from (e.g., thicker than) the anodes 121A-121D and cathodes 122A-122D. As show, the device 100 is devoid of any anode or cathode arranged on, or extending laterally beyond, any side wall 113-116 of the LED device 100.

FIG. 10F is a right side elevation view of the first subassembly 100-3 illustrated FIG. 10B, being devoid of a lens but showing solid state emitter chips 150B, 150D and wirebonds 152 arranged over a top surface 111 of the substrate 110.

FIG. 10G is a side cross-sectional view of the third subassembly 100-2 of FIG. 10D, taken along section lines "A"-"A" depicted in FIG. 10E. FIG. 10G illustrates electrically vias 125C, 125D defined through the substrate 110 between the top and bottom surfaces 111, 112, and arranged to provide electrical communication between top side traces (die attach pads) 141C, 14D and bottom side traces (anodes) 121C, 121D. The thermal element 112 is further illustrated along the bottom surface 112 of the substrate 110. As shown in FIG. 10G, the upper solder mask 147 may extend laterally past the top side traces 140 but not quite to side edges 113, 115 of the substrate 110.

FIG. 10H is an exploded right side elevation view of the emitter package 100, separately depicting the lens 160 registered with the first subassembly 100-3 of FIG. 10B. FIG. 10I is another perspective view of the emitter package 100. Although FIGS. 10H-10I illustrate the lens 160 as including a hemispherical central raised portion 161, it is to be appreciated that any suitable lens shape (including raised, flat, or recessed shapes) may be provided in various embodiments. The lens 160 is preferably molded and may either be molded in place over the emitter chips 150A-150D and substrate 110, or may be pre-molded and then affixed to a subassembly including the substrate 110 and emitter chips 150A-150D.

FIG. 11A illustrates a lighting apparatus 1100 including first and second LED components 1101, 1102 supported in or on a substrate or other body structure 1109. The first and the second LED components 1101, 1102 each include at least one LED chip (optionally multiple LED chips 1103A-1103B, 1104A-1104B). In certain embodiments, at least one LED chip 1103A-1103B, 1104A-1104B of each LED component 1101, 1102 is preferably arranged to stimulate emissions of one or more lumiphoric materials 1105A, 1106A. Although FIG. 11A illustrates two LED chips 1103A-1103B, 1104A-1104B as being associated with each LED component 1101, 1102, it is to be appreciated that any suitable number of one or more (e.g., one, two, three, four, five, six, etc.) LED chips may be associated with one or more LED components in certain embodiments. The first and second LED components 1101, 1102 may embody any suitable LED components, features, and/or capabilities as described herein, and are preferably separately controllable (e.g., in order to adjust melatonin suppression characteristics of combined emissions of the lighting apparatus 1100). In certain embodiments, each LED within a single LED component may be individually controlled, or groups of two or more LEDs within a single component may be controlled as a group.

Figure 11B:
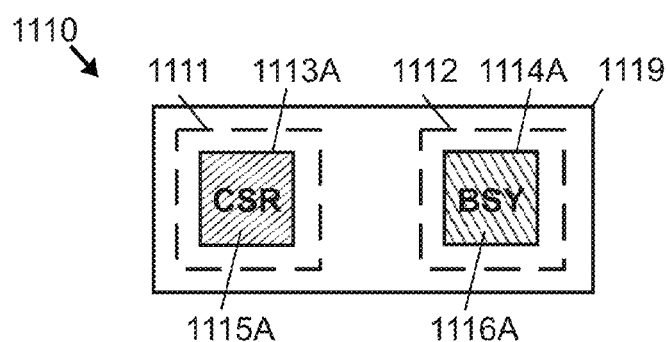

FIG. 11B illustrates a lighting apparatus 1110 including first and second LED components 1111, 1112 supported in or on a substrate or other body structure 1119. The first LED component 1111 includes a first (e.g., cyan) LED 1113A arranged to stimulate emissions of at least one first (e.g., red) lumiphoric material 1115A, and the second LED component 1112 includes a second (e.g., blue) LED 1114A arranged to stimulate emissions of at least one second (e.g., yellow) lumiphoric material 1116A. The first and second LED components 1111, 1112 may embody any suitable LED components, features, and/or capabilities as described herein, and are preferably separately controllable (e.g., in order to adjust melatonin suppression characteristics of combined emissions of the lighting apparatus 1110). In certain embodiments, additional or different LEDs and/or lumiphors may be associated with one or more of the LED components 1111, 1112, and/or one or more additional LED components may be provided.

Figure 11C:
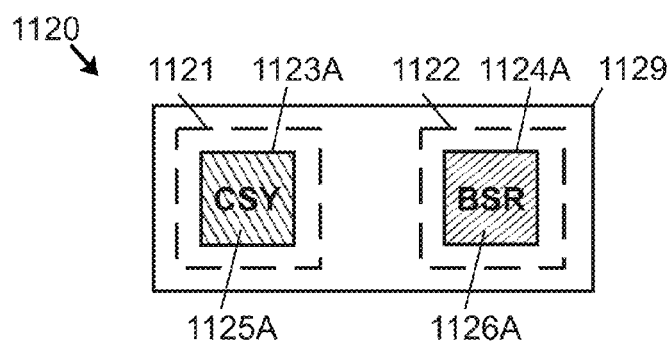

FIG. 11C illustrates a lighting apparatus 1120 including first and second LED components 1121, 1122 supported in or on a substrate or other body structure 1129. The first LED component 1121 includes a first (e.g., cyan) LED 1123A arranged to stimulate emissions of at least one first (e.g., yellow) lumiphoric material 1125A, and the second LED component 1122 includes a second (e.g., blue) LED 1124A arranged to stimulate emissions of at least one second (e.g., red) lumiphoric material 1126A. The first and second LED components 1121, 1122 may embody any suitable LED components, features, and/or capabilities as described herein, and are preferably separately controllable (e.g., in order to adjust melatonin suppression characteristics of combined emissions of the lighting apparatus 1120). In certain embodiments, additional or different LEDs and/or lumiphors may be associated with one or more of the LED components 1121, 1122, and/or one or more additional LED components may be provided.

Figure 11D:
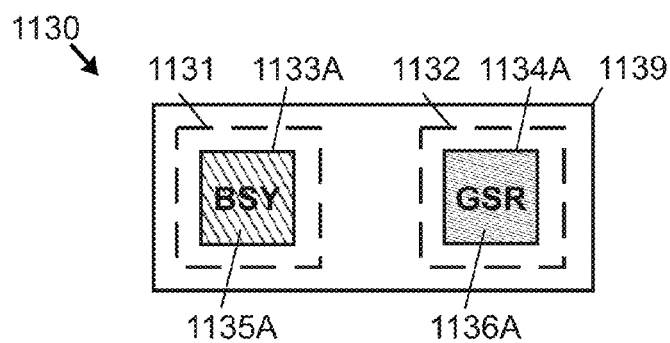

FIG. 11D illustrates a lighting apparatus 1130 including first and second LED components 1131, 1132 supported in or on a substrate or other body structure 1139. The first LED component 1131 includes a first (e.g., blue) LED 1133A arranged to stimulate emissions of at least one first (e.g., yellow) lumiphoric material 1135A, and the second LED component 1132 includes a second (e.g., green) LED 1134A arranged to stimulate emissions of at least one second (e.g., red) lumiphoric material 1136A. The first and second LED components 1131, 1132 may embody any suitable LED components, features, and/or capabilities as described herein, and are preferably separately controllable (e.g., in order to adjust melatonin suppression characteristics of combined emissions of the lighting apparatus 1130). In certain embodiments, additional or different LEDs and/or lumiphors may be associated with one or more of the LED components 1131, 1132, and/or one or more additional LED components may be provided.

FIG. 11E illustrates a lighting apparatus 1140 including first and second LED components 1141, 1142 supported in or on a substrate or other body structure 1149. The first LED component 1141 includes a first (e.g., blue) LED 1143A arranged to stimulate emissions of at least one first (e.g., yellow) lumiphoric material 1145A. The second LED component 1142 includes a second (e.g., blue) LED 1144A arranged to stimulate emissions of at least one second (e.g., yellow) lumiphoric material 1146A. Preferably, the peak wavelength and/or full-width half-max characteristics differ significantly between the first and second LEDs 1143A, 1144A, and/or between the first and second lumiphoric materials 1145A, 1146A, in order to confer different melatonin suppression characteristics. For example, the peak wavelengths of the first and second LEDs (or of the first and second lumiphoric materials 1145A, 1146A) may differ by threshold values of at least about 10 nm, at least about 20 nm, at least about 30 nm or some other suitable value; and FWHM values of the first and second LEDs (or of the first and second lumiphoric materials 1145A, 1146A) may differ by 10%, 20%, 30%, or some other suitable value. The first and second LED components 1141, 1142 may embody any suitable LED components, features, and/or capabilities as described herein, and are preferably separately controllable (e.g., in order to adjust melatonin suppression characteristics of combined emissions of the lighting apparatus 1140). In certain embodiments, additional or different LEDs and/or lumiphors may be associated with one or more of the LED components 1141, 1142, and/or one or more additional LED components may be provided.

FIG. 11F illustrates a lighting apparatus 1150 similar to that described above in connection with FIG. 11E, with the addition of multiple (e.g., yellow and red) lumiphoric materials to each solid state emitter. The apparatus 1150 includes first and second LED components 1151, 1152 supported in or on a substrate or other body structure 1159. The first LED component 1151 includes a first (e.g., blue) LED 1153A arranged to stimulate emissions of multiple first (e.g., yellow and red) lumiphoric materials 1155A. The second LED component 1152 includes a second (e.g., blue) LED 1154A arranged to stimulate emissions multiple second (e.g., yellow and red) lumiphoric materials 1156A. Preferably, the peak wavelength and/or full-width half-max characteristics differ significantly between the first and second LEDs 1153A, 1154A, and/or between corresponding components of the first and second lumiphoric materials 1155A, 1156A, in order to confer different melatonin suppression characteristics. The first and second LED components 1151, 1152 may embody any suitable LED components, features, and/or capabilities as described herein, and are preferably separately controllable (e.g., in order to adjust melatonin suppression characteristics of combined emissions of the lighting apparatus 1150). In certain embodiments, additional or different LEDs and/or lumiphors may be associated with one or more of the LED components 1151, 1152, and/or one or more additional LED components may be provided FIG. 11G illustrates a lighting apparatus 1160 including first and second LED components 1161, 1162 supported in or on a substrate or other body structure 1169. The first LED component 1161 includes a first (e.g., blue) LED 1163A arranged to stimulate emissions of at least one first (e.g., cyan) lumiphoric material 1165A, in combination with an additional (e.g., red) LED 1163B. The second LED component 1162 includes a second (e.g., blue) LED 1164A arranged to stimulate emissions of at least one second (e.g., yellow) lumiphoric material 1166A. The first and second LED components 1161, 1162 may embody any suitable LED components, features, and/or capabilities as described herein, and are preferably separately controllable (e.g., in order to adjust melatonin suppression characteristics of combined emissions of the lighting apparatus 1160). In certain embodiments, additional or different LEDs and/or lumiphors may be associated with one or more of the LED components 1161, 1162, and/or one or more additional LED components may be provided.

FIG. 11H illustrates a lighting apparatus 1170 including first and second LED components 1171, 1172 supported in or on a substrate or other body structure 1179. The first LED component 1171 includes a first (e.g., blue) LED 1173A arranged to stimulate emissions of at least one first (e.g., cyan) lumiphoric material 1175A, in combination with an additional (e.g., green) LED 1173B arranged to stimulate emissions of at least one additional (e.g., red) lumiphoric material 1175B. The second LED component 1172 includes a second (e.g., blue) LED 1174A arranged to stimulate emissions of at least one second (e.g., yellow) lumiphoric material 1176A. The first and second LED components 1171, 1172 may embody any suitable LED components, features, and/or capabilities as described herein, and are preferably separately controllable (e.g., in order to adjust melatonin suppression characteristics of combined emissions of the lighting apparatus 1160). In certain embodiments, additional or different LEDs and/or lumiphors may be associated with one or more of the LED components 1171, 1172, and/or one or more additional LED components may be provided.

Although the FIGS. 11A-11H illustrate use of LEDs having peak wavelengths in the visible range, it is to be appreciated that LEDs having peak wavelengths in a non-visible range (e.g., ultraviolet LEDs) may be substituted, in combination with appropriate lumiphors to provide desired spectral output characteristics.

FIG. 12 illustrates interconnections between various components of a light emitting apparatus 1200 including first and second LED components 1201, 1202 arranged in series, with at least one control circuit 1210 arranged to control modulation of current and/or duty cycle of the LED components 1201, 1202 using controllable bypass and/or shunt elements 1211, 1212. The at least one control circuit 1210 may be controlled responsive to one or more user input elements 1206, one or more timer or clock elements 1207, and/or one or more sensor elements 1208 (e.g., temperature sensing element, photosensors, etc.). Various components of the light emitting apparatus 1200 may be supported by, arranged on, or arranged in electrical communication portions of a substrate or support element 1209. In operation, current is applied to the lighting apparatus 1200 between anode 1221A and cathode 1221B. Supply of current to, and/or duty cycle of, a first LED component 1201 may be controlled with a first controllable bypass or shunt element 1211. Similarly, supply of current to, and/or duty cycle of, a second LED component 1202 may be controlled with a second controllable bypass or shunt element 1212, with the second LED component 1202 arranged in series with the first LED component 1201. Each of the first and second controllable bypass or shunt elements 1211, 1212 may be controlled by at least one control circuit 1210, optionally in response one or more user input elements 1206, one or more timer or clock elements 1207, and/or one or more sensor elements 1208.

FIG. 13 illustrates interconnections between various components of a light emitting apparatus 1300 including first and second LED components 1301, 1302 arranged in parallel, with at least one control circuit 1310 (e.g., optionally including control circuit portions 1310A, 1310B) arranged to control modulation of current and/or duty cycle of the LED components 1301, 1302 using controllable bypass and/or shunt elements 1311, 1312. The at least one control circuit 1310 may be controlled responsive to one or more user input elements 1306, one or more timer or clock elements 1307, and/or one or more sensor elements 1308. Various components of the light emitting apparatus 1300 may be supported by, arranged on, or arranged in electrical communication portions of a substrate or support element 1309. In operation, current may be supplied to the first LED component 1301 via a first anode 1321A and cathode 1321B, wherein supply of current to, and/or duty cycle of, the first LED component 1301 may be modulated with a first controllable bypass or shunt element 1311. In a like manner, current may be supplied to the second LED component 1302 via a second anode 1322A and cathode 1322B, wherein supply of current to, and/or duty cycle of, the second LED component 1302 may be modulated with a second controllable bypass or shunt element 1312. The first and second controllable bypass or shunt elements 1311, 1312 may be controlled by at least one control circuit 1310 (optionally with dedicated circuit portions 1310A, 1310B), optionally in response one or more user input elements 1306, one or more timer or clock elements 1307, and/or one or more sensor elements 1308.

FIG. 14 illustrates a lighting apparatus (e.g., light fixture) 1410 according to at least one embodiment. The apparatus 1400 includes a substrate or mounting plate 1475 to which multiple solid state emitter (e.g., LED) lamps 1470-1 to 1470-6 (with at least some lamps 1470-1 to 1470-6 optionally embodying a multi-chip lamp such as a multi-chip LED package) are attached, wherein each lamp 1470-1 to 1470-6 embodies at least on LED component as described herein. Although the mounting plate 1475 is illustrated as having a circular shape, the mounting plate may be provided in any suitable shape or configuration (including non-planar and curvilinear configurations). Different solid state emitter chips within a single multi-chip solid state emitter lamp may be configured to emit the same or different colors (e.g., wavelengths) of light. With specific reference to a first solid state lamp 1470-1, each solid state lamp 1470-1 to 1470-6 may include multiple solid state emitters (e.g., LEDs) 1474A-1474C preferably arranged on a single submount 1461. Although FIG. 14 illustrates four solid state emitter chips as being associated with each multi-chip solid state lamp 1470-1 to 1470-6, it is to be appreciated that any suitable number of solid state emitter chips may be associated with each multi-chip solid state lamp 1470-1 to 1470-6, and the number of solid state emitter chips associated with different (e.g., multi-chip) solid state lamps may be different. Each solid state lamp in a single fixture 1410 may be substantially identical to one another, or solid state lamps with different output characteristics may be intentionally provided in a single fixture 1410.

The solid state lamps 1470-1 to 1470-6 may be grouped on the mounting plate 1475 in clusters or other arrangements so that the light fixture 1410 outputs a desired pattern of light. In certain embodiments, at least one state emitter lamp associated with a single fixture 1410 includes a lumiphor-converted light emitting component (e.g., BSY, BSC, BS(Y+R), CSR, CSY, GSR, UVSC, etc. emitter). In certain embodiments, multiple LED components having different melatonin suppression effects in the apparatus 1410 may be separately controlled separately, to permit aggregated melatonin suppression effect of the lighting device to be adjusted, preferably wherein such adjustment of melatonin suppression effect may be accompanied by small or minimal change in corrected color temperature.

With continued reference to FIG. 14, the light fixture 1410 may include one or more control circuit components 1480 arranged to operate the lamps 1470-1 to 1470-6 by independently applying currents and/or adjusting duty cycle of respective LED components. In certain embodiments, individual solid state chip 1464A-1464D in various lamps 1470-1 to 1470-6 may be configured to be individually addressed by the control circuit 1480. In certain embodiments, the lighting apparatus 1410 may be self-ballasted. In certain embodiments, a control circuit 1480 may include a current supply circuit configured to independently apply an on-state drive current to each individual solid state chip responsive to a control signal, and may include one or more control elements configured to selectively provide control signals to the current supply circuit. As solid state emitters (e.g., LEDs) are current-controlled devices, the intensity of the light emitted from an electrically activated solid state emitter (e.g., LED) is related to the amount of current with which the device is driven. A common method for controlling the current driven through an LED to achieve desired intensity and/or color mixing is a Pulse Width Modulation (PWM) scheme, which alternately pulses the LEDs to a full current "ON" state followed by a zero current "OFF" state. The control circuit 1480 may be configured to control the current driven through the solid state emitter chips 1464A-1464D associated with the lamps 1470-1 to 1470-6 using one or more control schemes known in the art. The control circuit 1480 may be attached to an opposite or back surface of the mounting plate 1475, or may be provided in an enclosure or other structure (not shown) that is segregated from the lighting device 1400.

While not illustrated in FIG. 14, the light fixture 1410 a may further include one or more heat spreading components and/or heatsinks for spreading and/or removing heat emitted by solid state emitter chips 1464A-1464D associated with the lamps 1470-1 to 1470-6. For example, a heat spreading component may include a sheet of thermally conductive material configured to conduct heat generated by the solid state emitter chips 1464A-1464D of the light fixture 1410 and spread the conducted heat over the area of the mounting plate 1475 to reduce thermal stratification in the light fixture 1410. A heat spreading component may be embodied in a solid material, a honeycomb or other mesh material, an anisotropic thermally conductive material (e.g., graphite), one or more fins, and/or other materials or configurations.

FIG. 15 illustrates a lighting apparatus (e.g., light fixture) 1510 according to at least one embodiment. The apparatus includes multiple solid state emitter lamps 1500A-1500X (which may optionally be embodied in solid state emitter packages) each including multiple solid state light emitting chips (e.g., LEDs) 1548A-1548X—with each lamp 1500A-1500X embodying one or more LED components as described previously herein. Each lamp 1500A-1500X preferably includes multiple emitters arranged to generate spectral output including different peak wavelengths. (Although six lamps 1500A-1500X are shown, it is to be appreciated that any desirable number of clusters may be provided, as represented by the variable "X"). In certain embodiments, each lamp 1500A-1500X may embody an individually temperature compensated lamp. Each lamp 1500A-1500X may preferably (but not necessarily) include a single submount 1542A-1542X to which the multiple LEDs 1548A-1548X are mounted or otherwise supported. The lighting device 1510 includes a body structure or substrate 1511 to which each lamp 1500A-1500X may be mounted, with each cluster 1500A-1500X optionally being arranged in conductive thermal communication with a single heatsink 1518 and further arranged to emit light to be diffused by a single diffuser or other optical element 1517. The lighting device 1510 is preferably self-ballasted. Power may be supplied to the lighting device via contacts 1516 (e.g., as may be embodied in a single anode and single cathode, or multiple anodes and cathodes). A power conditioning circuit 1512 may provide AC/DC conversion utility, voltage conversion, and/or filtering utility. At least control circuit 1514 may be provided to control operation (e.g., control dimming) of one or more lamps 1500A-1500X or subgroups thereof. In certain embodiments, each lamp 1500A-1500X may include one or more emitters of a first LED component and one or more emitters of a second LED component. In other embodiments, each lamp 1500A-1500X may include emitters of either a first LED component or a second LED component, but not emitters of both LED components within the same specific lamp 1500A-1500X. In one or more photosensors or light sensing elements (not shown) may be arranged to receive emissions from one or more clusters 1500A-1500X, with an output signal of the one or more light sensing elements being used to control or adjust operation of the clusters 1500A-1500X, such as to ensure attainment of a desired output color or output color temperature by the clusters 1500A-1500X. In certain embodiments, multiple LED components having melatonin suppression characteristics in the apparatus 1510 may be separately controlled separately, to permit melatonin suppression effect of the lighting device to be adjusted, preferably wherein such adjustment of melatonin suppression effect may be accompanied by small or minimal change in corrected color temperature.

In certain embodiments, two or more solid state emitter (e.g., LED) components as described herein may be embodied in backlights for display panels. Various embodiments including backlights are illustrated in FIGS. 16-18.

FIG. 16 is a perspective assembly view of a display device 1600 including a substrate 1601 supporting multiple solid state emitting elements 1604A-1604X constituting a backlight illuminate (e.g., directly backlight) a display (e.g., LCD) panel 1609, such as may be arranged to display text, images, and/or graphics. (Although FIG. 16 shows the display device 1600 having thirty-two solid state light emitters, it will be readily apparent to one skilled in the art that any suitable number of emitters may be provided. For this reason, the designation "X" is used to represent the last element in a series, with the understanding that the suffix "X" in such context represents a variable that could represent any desired number of elements.) In certain embodiments, each light emitting element 1604A-1604X comprises a first or a second LED component as described herein, arranged to have the same or similar chromaticities but being controllable to permit adjustment of melatonin suppression effects. In certain embodiments, each light emitting element 1604A-1604X comprises a first and a second LED component as outlined above. In certain embodiments, each solid state light emitting element 1604A-1604X comprises a multi-chip solid state emitter package. Multiple emitters in a multi-chip solid state emitter package (and multiple LED within a LED component) may be independently controlled. In certain embodiments, individual solid state emitting elements or groups of solid state emitting elements 1604A-1604X may be independently controlled with respect to at least one of melatonin suppression characteristics, intensity, color, and color temperature. Independent control of different solid state emitter elements 1604A-1604X may be used to provide local dimming and/or local coloring/color enhancement.

FIG. 17 is a perspective assembly view of a display device 1700 including a backlight waveguide 1711 arranged to be lit along edges thereof by multiple solid state light emitting elements 1704A-1704X, 1705A-1705X as described herein, with the backlight waveguide 1711 arranged to illuminate (e.g., backlight) a display panel such as a LCD panel. Although FIG. 17 illustrates only two edges of the waveguide 1711 as having associated light emitting elements 1704A-1704X, 1705A-1705X, it is to be understood that all four edges of the waveguide 1711 may have associated solid state light emitting components. In certain embodiments, each light emitting element 1704A-1704X, 1705A-1705X comprises a first or a second LED component as described herein, which have the same or similar chromaticities but are controllable to permit adjustment of melatonin suppression effects. In certain embodiments, each light emitting element 1704A-1704X, 1705A-1705X comprises a first and a second LED component as outlined above. In certain embodiments, each solid state light emitting element 1704A-1704X, 1705A-1705X comprises a multi-chip solid state emitter package. Multiple emitters in a multi-chip solid state emitter package (and multiple LED within a LED component) may be independently controlled. In certain embodiments, individual solid state emitting elements or groups of solid state emitting elements 1704A-1704X, 1705A-1705X may be independently controlled with respect to at least one of melatonin suppression characteristics, intensity, color, and color temperature. Independent control of different solid state emitter elements 1704A-1704X, 1705A-1705X may be used to provide local dimming and/or local coloring/color enhancement.

FIG. 18 is a schematic view of a light emitting group or array 1800 including solid state emitter (e.g., LED) components 1801A-1801X as described herein, optionally supported by a substrate 1807, and in communication with at least one controller 1808 and/or timer/clock 1814 or other control device. The controller 1808, which preferably includes a microprocessor arranged to implement a machine-readable instruction set, is arranged to receive power from a power source 1812. Operation of the lighting device 1800 may optionally be responsive to at least one output signal of one or more sensors 1813 (e.g., arranged to sense electrical, optical, and/or thermal properties and/or environmental conditions) in communication with the controller 1808. Operation of the lighting device 1800 may optionally be responsive to an output signal of a timer or clock 1814. For example, a timer (or alternatively a clock) 1814 may be arranged to trigger switching between a first operating mode and a second operating mode, wherein in the first and second operating modes the combined emissions of the first LED component and second LED component provide the same or similar chromaticities (e.g., each having a CCT within a specified number of MacAdam ellipses of a target CCT), but have melatonin suppression effects that differ by a predetermined threshold (e.g., at least about 5%, 10%, 15%, 20% 25%, 30%, 35%, 40%, 50% or more). Each solid state emitter component 1801A-1801X, and preferably different solid state emitters within or associated with each solid state emitter component, may be independently controlled. Although FIG. 18 illustrates each lamp 1801A-1801X as being supported by a common substrate 1807, in certain embodiments, different lighting devices of an array or group 1800 may be supported on different substrates optionally spatially segregated from one another. The controller 1808 or other control element may be integrated with a lighting device 1800 including one or more of the solid state emitter components 1801A-1801X, or the controller 1808 may be located remotely from the solid state emitter components 1801A-1801X. In certain embodiments, the controller 1808 may include a communication element (not shown) arranged to receive signals from a network, remote device, or wireless link to affect control or operation of the lamps 1801A-1801X. The array or group 1800 may comprise a backlight, light fixture, group of lighting devices or light fixtures, or other desirable implementation as described or suggested herein.

Embodiments as disclosed herein may provide one or more of the following beneficial technical effects: permitting adjustment of melatonin suppression characteristics of lighting devices; permitting adjustment of melatonin suppression characteristics of lighting devices while maintaining acceptably high CRI for a desired end use; permitting adjustment of correlated color temperature and also permitting adjustment of melatonin suppression characteristics at different CCT; and permitting a user to identify a specified time period for switching between melatonin suppressing effects of backlights and backlit electronic devices. Such effects may ameliorate or reduce symptoms of circadian rhythm disorders or other health conditions, avoid interference with sleep cycles, and/or enhance nighttime worker alertness and performance.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein. Correspondingly, the invention as hereinafter claimed is intended to be broadly construed and interpreted, as including all such variations, modifications and alternative embodiments, within its scope and including equivalents of the claims.

What is claimed is:

1. An illuminated display device comprising:
   a display panel configured to display at least one of images or text; and
   a backlight arranged to illuminate the display panel, wherein the backlight comprises:
   a first LED component;
   a second LED component; and
   a timer or clock arranged to trigger switching between a first operating mode and a second operating mode;
   wherein in the first operating mode the first LED component and the second LED component generate combined emissions that (i) are within six MacAdam ellipses of a target correlated color temperature, and (ii) embody a first melatonin suppression milliwatt per hundred lumens value; and
   wherein in the second operating mode the first LED component and the second LED component generate combined emissions that (i) are within six MacAdam ellipses of the target correlated color temperature, and (ii) embody a second melatonin suppression milliwatt per hundred lumens value that is at least about 10 percent greater than the first melatonin suppression milliwatt per hundred lumens value.

2. The illuminated display device according to claim 1, wherein the display panel comprises a liquid crystal display (LCD) panel.

3. The illuminated display device according to claim 1, wherein in the first operating mode the first LED component and the second LED component generate combined emissions that are within four MacAdam ellipses of the target correlated color temperature, and wherein in the second operating mode the first LED component and the second LED component generate combined emissions that are within four MacAdam ellipses of the target correlated color temperature.

4. The illuminated display device according to claim 3, wherein at least one of the first LED component or the second LED component comprises at least one LED arranged to stimulate emissions of at least one lumiphoric material.

5. The illuminated display device according to claim 3, wherein the first LED component comprises at least one first LED arranged to stimulate emissions of at least one first lumiphoric material, and wherein the second LED component comprises at least one second LED arranged to stimulate emissions of at least one second lumiphoric material.

6. The illuminated display device according to claim 3, wherein the timer or clock comprises a user-adjustable timer.

7. The illuminated display device according to claim 3, further comprising at least one control circuit arranged to adjust supply of current to at least one of the first LED component or the second LED component to operate the first LED component and the second LED component according to the first operating mode or the second operating mode.

8. The illuminated display device according to claim 3, wherein the second melatonin suppression milliwatt per hundred lumens value is at least about 30 percent greater than the first melatonin suppression milliwatt per hundred lumens value.

9. The illuminated display device according to claim 3, wherein the target correlated color temperature comprises a value selected from a range of from about 2500K to about 6000K.

10. An electronic device comprising the illuminated display device according to claim 3.

11. A light emitting apparatus comprising:
    a first LED component;
    a second LED component; and
    at least one of a timer, a clock, a user input element, or a sensor element;
    wherein the first LED component and the second LED component are arranged to be operated in a first operating mode in which combined emissions of the first LED component and the second LED component embody a first melatonin suppression milliwatt per hundred lumens value;
    wherein the first LED component and the second LED component are arranged to be operated in a second operating mode in which combined emissions of the first LED component and the second LED component embody a second melatonin suppression milliwatt per hundred lumens value that is at least about 10 percent greater than the first melatonin suppression milliwatt per hundred lumens value; and
    wherein the light emitting apparatus is arranged to trigger switching between the first operating mode and the second operating mode responsive to an output signal of the at least one of a timer, a clock, a user input element, or a sensor element.

12. The light emitting apparatus of claim 11, wherein:
    in the first operating mode, the combined emissions of the first LED component and the second LED component are within six MacAdam ellipses of a target correlated color temperature; and
    in the second operating mode, the combined emissions of the first LED component and the second LED component are within six MacAdam ellipses of the target correlated color temperature.

13. The light emitting apparatus of claim 11, wherein the at least one of a timer, a clock, a user input element, or a sensor element comprises a timer or a clock.

14. The light emitting apparatus of claim 11, wherein the at least one of a timer, a clock, a user input element, or a sensor element comprises a user input element.

15. The light emitting apparatus of claim 11, wherein the at least one of a timer, a clock, a user input element, or a sensor element comprises a sensor element.

16. The light emitting apparatus of claim 15, wherein the sensor element comprises a temperature sensor.

17. The light emitting apparatus of claim 15, wherein the sensor element comprises a photosensor or a light sensing element.

18. The light emitting apparatus of claim 15, wherein the sensor element is arranged to sense at least one environmental condition.

19. The light emitting apparatus of claim 11, wherein at least one of the first LED component or the second LED component comprises at least one LED arranged to stimulate emissions of at least one lumiphoric material.

20. The light emitting apparatus of claim 11, wherein combined emissions of the first LED component and the second LED component, when operated in the first operating mode, embody a color rendering index (CRI) value of at least about 80.

21. A light emitting apparatus comprising:
a first LED component;
a second LED component; and
a control device;
wherein the control device is arranged to operate the first LED component and the second LED component in a first operating mode in which combined emissions of the first LED component and the second LED component (i) are within six MacAdam ellipses of a target correlated color temperature, and (ii) embody a first melatonin suppression milliwatt per hundred lumens value;
wherein the control device is arranged to operate the first LED component and the second LED component in a second operating mode in which combined emissions of the first LED component and the second LED component (i) are within six MacAdam ellipses of the target correlated color temperature, and (ii) embody a second melatonin suppression milliwatt per hundred lumens value that is at least about 10 percent greater than the first melatonin suppression milliwatt per hundred lumens value; and
wherein the light emitting apparatus comprises at least one of the following features (a) to (c):
(a) at least one of the first LED component or the second LED component comprises at least one LED arranged to stimulate emissions of at least one lumiphoric material;
(b) combined emissions of the first LED component and the second LED component, when operated in the first operating mode, embody a color rendering index (CRI) value of at least about 80; or
(c) the light emitting apparatus comprises at least one element selected from the group consisting of a timer, a clock, a photosensor, and at least one user input element, wherein the at least one element is arranged to trigger switching between the first operating mode and the second operating mode.

* * * * *

UNITED STATES PATENT AND TRADEMARK OFFICE
CERTIFICATE OF CORRECTION

PATENT NO.         : 9,661,715 B2                                          Page 1 of 1
APPLICATION NO.    : 14/662608
DATED              : May 23, 2017
INVENTOR(S)        : Antony Paul van de Ven and Paul Kenneth Pickard It is certified that error appears in the above-identified patent and that said Letters Patent is hereby corrected as shown below:

In the Specification

In Column 8, Lines 52, 60, 63, and 64-65, replace "msm/100 I" with --msm/100 l--.

In Column 9, Lines 2, 3, 4, 17, 22, and 25-26, replace "msm/100 I" with --msm/100 l--.

In Column 16, Lines 53, 54, 55, 56, 57-58, 58, 63 (twice), 65, and 66, replace "msm/100 I" with --msm/100 l--.

In Column 20, Line 36, replace "msm/100 I" with --msm/100 l--.

In Column 22, Lines 30 and 34, replace "msm/100 I" with --msm/100 l--.

In Column 23, Lines 33, 44, 62, and 66, replace "msm/100 I" with --msm/100 l--.

In Column 24, Lines 4, 10, 12, 18, 34, 40, 46, 47, 54, 59, 61, and 62, replace "msm/100 I" with --msm/100 l--.

In Column 25, Lines 4, 25, 27, and 28, replace "msm/100 I" with --msm/100 l--.

Signed and Sealed this
Fifteenth Day of August, 2017

Joseph Matal
*Performing the Functions and Duties of the
Under Secretary of Commerce for Intellectual Property and
Director of the United States Patent and Trademark Office*